United States Patent

Higuchi et al.

Patent Number: 5,081,284
Date of Patent: Jan. 14, 1992

[54] PROTEINASE INHIBITOR

[75] Inventors: Naoki Higuchi; Masayuki Saitoh, both of Osaka; Norio Iwasawa, Kyoto; Motoo Sumida, Osaka; Hiroshi Shibata, Nara, all of Japan

[73] Assignee: Suntory Limited, Osaka, Japan

[21] Appl. No.: 373,811

[22] Filed: Jun. 29, 1989

[30] Foreign Application Priority Data

Apr. 10, 1989 [JP] Japan .................................. 1-89904

[51] Int. Cl.$^5$ ......................................... C07C 261/00
[52] U.S. Cl. .................. 560/159; 260/404.5; 548/477; 552/104; 556/420; 560/30; 560/31; 560/32; 560/148; 564/12; 564/87; 564/90; 564/91; 564/102; 564/154; 564/155; 564/164; 564/189
[58] Field of Search .............. 560/159, 30, 31, 32, 560/33, 148; 564/12, 91, 102, 154, 155, 159, 189; 548/477; 556/420; 260/389, 404.5

[56] References Cited
FOREIGN PATENT DOCUMENTS
1-121257 5/1989 Japan .

Primary Examiner—Michael L. Shippen
Attorney, Agent, or Firm—Cushman, Darby & Cushman

[57] ABSTRACT

A novel N-substituted peptidyl compound represented by the general formula (1):

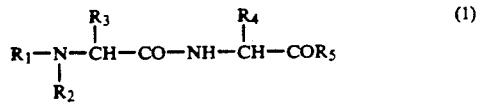

where $R_1$ is a straight-chained or branched acyl group having 2–10 carbon atoms, a branched, cyclic or partly branched cyclic alkyloxycarbonyl group having 4–15 carbon atoms, a substituted or unsubstituted benzyloxycarbonyl group, a 2,2,2-trichloroethyloxycarbonyl group, a 2-(trimethylsilyl)ethyloxycarbonyl group, a p-toluensulfonyl group, an o-nitrophenylsulfenyl group, a diphenylphosphonothioyl group, a triphenylmethyl group, a 2-benzoyl-1-methylvinyl group or a 4-phenylbutyryl group; $R_2$ is a hydrogen atom or when taken together with $R_1$, may form a phthaloyl group; $R_3$ is an isobutyl group, a n-butyl group or an isopropyl group; $R_4$ is a butyl group, a benzyl group or a methylthioethyl group; and $R_5$ is a hydrogen atom or a chloromethyl group, which inhibits the activity of cysteine proteinases.

2 Claims, No Drawings

PROTEINASE INHIBITOR

FIELD OF THE INVENTION

The present invention relates to novel N-substituted peptidyl compounds represented by the general formula (1) to be noted hereinafter. The present invention also relates to a cysteine proteinase inhibitor that contains a compound of the general formula (1) as an active ingredient and which shows strong enzyme inhibitory activity toward cysteine proteinases, in particular papain, calpain and even cathepsin.

PRIOR ART

Drugs that specifically inhibit the activity of papain (E.C. 3.4.22.2) and calpain (E.C. 3.4.22.17), which are both cysteine proteinases, have the potential to be used as anti-inflammatories, so there has been a definite need for the development of such drugs. Calpain occurs extensively in mammals and birds and the predominant site of their presence is cytosol. Abnormal activation of this enzyme is considered to be responsible for the development of muscular dystrophy and cataracts. Cathepsin (E.C. 3.4.22.1) is a proteinase that is localized in lysosome and its abnormal activation seems to be responsible for cancer metastasis and for the development of muscular atrophy and muscular dystrophy. Hence, drugs that specifically inhibit the activity of calpain or cathepsin are desired for the purpose of developing therapeutic agents for muscular dystrophy, muscular atrophy and cataracts, as well as drugs capable of inhibiting cancer metastasis. As adjuncts to the efforts being made to develop these drugs, various cysteine proteinase inhibiting substances have been discovered (Shimizu, B. et al., J. Antibiot., 25, 515, 1972, Japanese Patent Public Disclosure Nos. 60-28990, 61-106600 and 61-103897). However, the inhibitors that have been known so far still leave room for improvement with respect to activity and transferrability into the body. Hence a particularly great need exists for the development of compounds that have a strong capability to inhibit cysteine proteinases including papain, calpain and cathepsin.

SUMMARY OF THE INVENTION

The present invention provides novel compounds having the ability to inhibit various cysteine proteinases including papain, calpain and cathepsin B.

The present invention also provides novel compounds that not only have inhibitory activity toward these enzymes but which are also suitable for various pharmaceutical uses by virtue of their good qualities with respect to transfer into the body.

DETAILED DESCRIPTION OF THE INVENTION

In accordance with the present invention, novel N-substituted peptidyl compounds having strong inhibitory activity toward cathepsin B, calpain or papain are provided, these compounds being represented by the general formula (1):

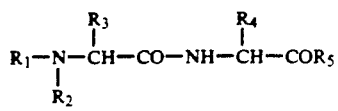

where $R_1$ is a straight-chained or branched acyl group having 2-10 carbon atoms, a branched, cyclic or partly branched cyclic alkyloxycarbonyl group having 4-15 carbon atoms, a substituted or unsubstituted benzyloxycarbonyl group, a 2,2,2-trichloroethyloxycarbonyl group, a 2-(trimethylsilyl)ethyloxycarbonyl group, a p-toluensulfonyl group, an o-nitrophenylsulfenyl group, a diphenylphosphonothioyl group, a triphenylmethyl group, a 2-benzoyl-1-methylvinyl group or a 4-phenylbutyryl group; $R_2$ is a hydrogen atom or when taken together with $R_1$, may form a phthaloyl group; $R_3$ is an isobutyl group, a n-butyl group or an isopropyl group; $R_4$ is a butyl group, a benzyl group or a methylthioethyl group; and $R_5$ is a hydrogen atom or a chloromethyl group.

The compounds of the present invention may be produced by various methods. To take as an example a compound of the general formula (1) where $R_5$ is a hydrogen atom and the group represented by $R_1$ or formed by $R_1$ when taken together with $R_2$ is stable against treatment with a base or a reducing agent, it may be readily produced by the following method: a compound represented by the general formula (2):

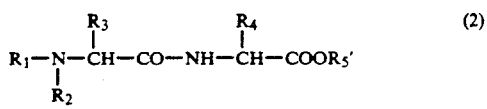

[where $R_1$, $R_2$, $R_3$ and $R_4$ each has the same meaning as defined for the general formula (1); and $R_5'$ is a lower alkyl group] is reduced to an alcoholic form in an organic solvent by treatment with a reducing agent, and the alcoholic form is oxidized to aldehyde by treatment with an oxidizer. To take as an example a compound of the general formula (1) where $R_5$ is a hydrogen atom and the group represented by $R_1$ or formed by $R_1$ when taken together with $R_2$ is unstable against treatment with a base or a reducing agent, it may be readily produced by the following method: a compound represented by the general formula (3):

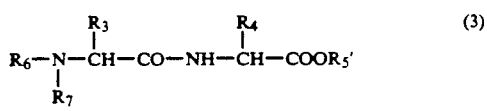

[where $R_3$, $R_4$ and $R_5'$ each has the same meaning as defined for the general formula (2); $R_6$ is an amino protecting group which is stable against treatment with a base or reduction with a reducing agent; $R_7$ is a hydrogen atom or, when taken together with $R_6$, forms an amino protecting group which is stable against treatment with a base or a reducing agent] is reduced to an alcoholic form in an organic solvent by treatment with a reducing agent, and after eliminating the protecting group $R_6$ or the protecting group formed by $R_6$ and $R_7$ taken together, a desired group $R_1$ or the group formed by $R_1$ and $R_2$ taken together is introduced into the amino group by an appropriate method, and the alcohol portion of the resulting compound is converted to aldehyde as in the method for preparing the previously described example of the compounds of formula (1).

Another compound of the general formula (1) wherein $R_5$ is a chloromethyl group may be produced by the following method: a carboxylic acid having OH in place of $R_5$ in the formula (1) is used as a starting material, which is converted to an activated ester in an organic solvent using ethyl chlorocarbonate or some other suitable compound, and diazomethane is allowed to act on the activated ester to form diazomethylketone, which is further treated with hydrochloric acid.

While various compounds are used as starting materials in the production of the compounds of the present invention, they are either known or capable of being readily synthesized by conventional methods.

The present invention is described hereinafter in greater detail with reference to examples and the results of inhibitory activity. It should, however, be noted that these examples are in no way intended to limit the technical scope of the present invention. In examples 1-18, $R_5$ in general formula (1) represents hydrogen. When sodium sulfate is used in Examples 1-27, it is anhydrous sodium sulfate. When the terms phenylbutyryl, caprylyl and caproyl are used in the specification, it should be understood that each of these groups can also be called phenylbutanoyl, octanoyl, and hexanoyl, respectively.

EXAMPLE 1

Production of N-caprylyl-L-leucyl-L-norleucinal [compound of formula (1) where $R_1=CH_3(CH_2)_6CO—$, $R_2=H—$, $R_3=(CH_3)_2CHCH_2—$, and $R_4=CH_3(CH_2)_3—$]

(a) Preparation of N-caprylyl-L-leucine

L-leucine (2.6 g) was dissolved in 1N NaOH (20 ml). To the ice-cooled solution, caprylyl chloride (3.3 ml) and 1N NaOH (20 ml) were added and the mixture was stirred at room temperature for 8 hours. After completion of the reaction, the reaction solution was washed with ether and 5N CHl was added to the aqueous phase to lower the pH to 2 or below and extraction was conducted with ethyl acetate. The extract was dried over sodium sulfate and the solvent was distilled off under reduced pressure. When the residue was subjected to recrystallization from a mixed solvent of ethyl acetate and hexane, the titled N-caprylyl-L-leucine (4.3 g, crystal) was obtained.

(b) Preparation of N-caprylyl-L-leucyl-L-norleucine methyl ester

N-caprylyl-L-leucine (2.6 g) prepared in step (a) and L-norleucine methyl ester hydrochloride (1.8 g) were dissolved in dry dimethylformamide (50 ml) and diethyl cyanophosphonate (1.6 g) was added to the solution. To the ice-cooled solution, triethylamine (2.0 g) was added and the mixture was stirred at room temperature for 12 hours. After completion of the reaction, water (200 ml) was added to the reaction solution, which was then subjected to extraction with ether. The organic layer was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-caprylyl-L-leucyl-L-norleucine methyl ester (2.2 g, oil) was obtained.

(c) Preparation of N-caprylyl-L-leucyl-L-norleucinol

N-caprylyl-L-leucyl-L-norleucine methyl ester (2.2 g) prepared in step (b) and sodium borohydride (1.0 g) were suspended in t-butyl alcohol (20 ml) and the suspension was refluxed under heating (90° C.) under nitrogen atmosphere. Absolute methanol (8 ml) was then added dropwise under reflux. After completion of the addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-caprylyl-L-leucyl-L-norleucinol (1.7 g, crystal) was obtained.

(d) Preparation of N-caprylyl-L-leucyl-L-norleucinal

N-caprylyl-L-leucyl-L-norleucinol (1.7 g) prepared in step (c) and triethylamine (2.0 g) were dissolved in anhydrous dimethyl sulfoxide (20 ml). To the resulting solution, a solution of sulfur trioxide-pyridine complex (3.0 g) in dimethyl sulfoxide (20 ml) was added. After being stirred at room temperature for 10 minutes, the mixture was poured into ice water (200 ml), followed by extractions with ethyl acetate three times, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-caprylyl-L-leucyl-L-norleucinal (1.0 g, crystal) was obtained as the end compound.

EXAMPLE 2

Production of N-caproyl-L-leucyl-L-norleucinal [compound of formula (1) where $R_1=CH_3(CH_2)_4CO—$, $R_2=H—$, $R_3=(CH_3)_2CHCH_2—$, and $R_4=CH_3(CH_2)_3—$]

(a) Preparation of N-caproyl-L-leucine

L-leucine (2.6 g) was dissolved in 1N sodium hydroxide (20 ml). To the ice-cooled solution, caproyl chloride (3.0 g) and 1N sodium hydroxide (20 ml) were added and the mixture was stirred at room temperature for 8 hours. After completion of the reaction, the reaction solution was washed with ether and 5N HCl was added to the aqueous phase to lower the pH to 2 or below and extraction was conducted with ethyl acetate. The extract was dried over sodium sulfate and the solvent was distilled off under reduced pressure. When the residue was subjected to recrystallization from a mixed solvent of ethyl acetate and hexane, the titled N-caproyl-L-leucine (2.8 g, crystal) was obtained.

(b) Preparation of N-caproyl-L-leucyl-L-norleucine methyl ester

N-caproyl-L-leucine (2.7 g) prepared in step (a) and L-norleucine methyl ester hydrochloride (2.2 g) were dissolved in dry methylformamide (50 ml) and diethyl cyanophosphonate (2.0 g) was added to the solution. To the ice-cooled solution, triethylamine (2.0 g) was added and the mixture was stirred at room temperature for 12 hours. After completion of the reaction, water (200 ml) was added to the reaction solution, which was then subjected to extraction with ether. The organic layer was washed successively with 1N HCl, brine, saturated sodium hydrogencarbonate, and brine, followed by drying over sodium sulfate. Thereafter, the solvent was distilled off under reduced pressure. When the residue was purified by medium-pressure column chromatography using silica gel, the titled N-caproyl-L-leucyl-L-norleucine methyl ester (2.2 g, oil) was obtained.

(c) Preparation of N-caproyl-L-leucyl-L-norleucinol

N-caproyl-L-leucyl-L-norleucine methyl ester (2.2 g) prepared in step (b) and sodium borohydride (1.0 g) were suspended in t-butyl alcohol (20 ml) and the suspension was refluxed under heating (90° C.) under nitrogen atmosphere. Absolute methanol (8 ml) was then added dropwise under reflux. After completion of the addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was subjected to recrystallization from a mixed solvent of ethyl acetate and hexane, whereupon the titled N-caproyl-L-leucyl-L-norleucinol (1.6 g, crystal) was obtained.

(d) Preparation of N-caproyl-L-leucyl-L-norleucinal

N-caproyl-L-leucyl-L-norleucinol (1.6 g) prepared in step (c) and triethylamine (2.0 g) were dissolved in anhydrous dimethyl sulfoxide (15 ml). To the resulting solution, a solution of sulfur trioxide-pyridine complex (3.0 g) in dimethyl sulfoxide (15 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was purified by medium-pressure column chromatography using silica gel, whereupon N-caproyl-L-leucyl-L-norleucinal (1.0 g, powder) was obtained as the end compound.

EXAMPLE 3

Production of N-isovaleryl-L-leucyl-L-norleucinal
[compound of formula (1) where
$R_1=(CH_3)_2CHCH_2CO-$, $R_2=H-$,
$R_3=(CH_3)_2CHCH_2-$, and $R_4=CH_3(CH_2)_3-$]

(a) Preparation of N-isovaleryl-L-leucine

L-leucine (5.2 g) was dissolved in 1N NaOH (40 ml). To the ice-cooled solution, isovaleryl chloride (2.4 g) and 1N NaOH (40 ml) were added and the mixture was stirred at room temperature for 8 hours. After completion of the reaction, the reaction solution was washed with ether and 5N HCl was added to the aqueous phase to lower the pH to 2 or below and extraction was conducted with ethyl acetate. The extract was dried over sodium sulfate and the solvent was distilled off under reduced pressure. When the residue was subjected to recrystallization from a mixed solvent of ethyl acetate and hexane, the titled N-isovaleryl-L-leucine (2.6 g, crystal) was obtained.

(b) Preparation of N-isovaleryl-L-leucyl-L-norleucine methyl ester

N-isovaleryl-L-leucine (2.6 g) prepared in step (a) and L-norleucine methyl ester hydrochloride (2.2 g) were dissolved in dry dimethylformamide (50 ml) and diethyl cyanophosphonate (2.0 g) was added to the solution. To the ice-cooled solution, triethylamine (2.0 g) was added and the mixture was stirred at room temperature for 12 hours. After completion of the reaction, water (200 ml) was added to the reaction solution, which was then subjected to extraction with ether. The organic layer was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-isovaleryl-L-leucyl-L-norleucine methyl ester (1.6 g, oil) was obtained.

(c) Preparation of N-isovaleryl-L-leucyl-L-norleucinol

N-isovaleryl-L-leucyl-L-norleucine methyl ester (1.6 g) prepared in step (b) and sodium borohydride (1.0 g) were suspended in t-butyl alcohol (30 ml) and the suspension was refluxed under heating (90° C.) under nitrogen atmosphere. Absolute methanol (5 ml) was then added dropwise under reflux. After completion of the dropwise addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was subjected to recrystallization from a mixed solvent of ethyl acetate and hexane, whereupon the titled N-isovaleryl-L-leucyl-L-norleucinol (1.2 g, crystal) was obtained.

(d) Preparation of N-isovaleryl-L-leucyl-L-norleucinal

N-isovaleryl-L-leucyl-L-norleucinol (1.0 g) prepared in step (c) and triethylamine (2.0 g) were dissolved in anhydrous dimethyl sulfoxide (15 ml). To the resulting solution, a solution of sulfur trioxide-pyridine complex (2.0 g) in dimethyl sulfoxide (15 ml) was added. After being stirred at room temperature for 10 minutes, the mixture was poured into ice water (200 ml), followed by extractions with ethyl acetate three times, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-isovaleryl-L-leucyl-L-norleucinal (0.7 g, crystal) was obtained as the end compound.

EXAMPLE 4

Production of N-(t-butyloxycarbonyl)-L-leucyl-L-norleucinal
[compound of formula (1) where $R_1=(CH_3)_3COCO-$,
$R_2=H-$, $R_3=(CH_3)_2CHCH_2-$, and
$R_4=CH_3(CH_2)_3-$]

(a) Preparation of N-(t-butyloxycarbonyl)-L-leucyl-L-norleucine methyl ester

N-(t-butyloxycarbonyl)-L-leucine monohydrate (2.5 g) was dissolved in dry methylene chloride (50 ml) and 1-ethyl-3-(3-dimethylaminopropyl)carbodiimide hydrochloride (1.2 g) was added to the solution. To the solution was further added a solution having L-norleucine methyl ester hydrochloride (1.8 g) and triethylamine (1.2 g) dissolved in dry methylene chloride (50 ml) and the mixture was stirred at room temperature for 6 hours. After completion of the reaction, the reaction solution was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-(t-butyloxycarbonyl)-t-leucyl-L-norleucine methyl ester (4.0 g, crystal) was obtained.

(b) Preparation of N-(t-butyloxycarbonyl)-L-leucyl-L-norleucinol

N-(t-butyloxycarbonyl)-L-leucyl-L-norleucine methyl ester (3.0 g) prepared in step (a) and sodium borohydride (1.0 g) were suspended in t-butyl alcohol (60 ml) and the suspension was refluxed (90° C.) under nitrogen atmosphere. Absolute methanol (10 ml) was then added dropwise under reflux. After completion of the dropwise addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-(t-butyloxycarbonyl)-L-leucyl-L-norleucinol (2.0 g, crystal) was obtained.

(c) Preparation of N-(t-butyloxycarbonyl)-L-leucyl-L-norleucinal

N-(t-butyloxycarbonyl)-L-leucyl-L-norleucinol (1.0 g) prepared in step (b) and triethylamine (1.2 g) were dissolved in anhydrous dimethyl sulfoxide (12 ml). To the resulting solution, a solution of sulfur trioxide-pyridine complex (2.0 g) in dimethyl sulfoxide (12 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-(t-butyloxycarbonyl)-L-leucyl-L-norleucinal (0.5 g, crystal) was obtained as the end compound.

EXAMPLE 5

Production of N-adamantyloxycarbonyl-L-leucyl-L-norleucinal [compound of formula (1) where $R_1$=Tricyclo[3,3,1,13,7]decane—OCO—, $R_2$=H—, $R_3$=(CH_3)_2CHCH_2—, and $R_4$=CH_3(CH_2)_3—]

(a) Preparation of N-adamantyloxycarbonyl-L-leucine

L-leucine (2.6 g) and potassium carbonate (7.0 g) were dissolved in water (100 ml). To the ice-cooled solution, adamantyloxycarbonyl fluoride (4.0 g) was added and the mixture was stirred at room temperature for 3 hours. After completion of the reaction, the reaction solution was washed with ether and 50% phosphoric acid was added to the aqueous phase to lower the pH to 2 or below and extraction was conducted with ether. The extract was dried over sodium sulfate and distilled off under reduced pressure. When the residue was subjected to recrystallization from a mixed solvent of ethyl acetate and hexane, the titled N-adamantyloxycarbonyl-L-leucine (3.6 g, crystal) was obtained.

(b) Preparation of N-adamantyloxycarbonyl-L-leucyl-L-norleucine methyl ester

N-adamantyloxycarbonyl-L-leucine (3.1 g) prepared in step (a) was dissolved in dry methylene chloride (50 ml) and 1-ethyl-3-(3-dimethylaminopropyl)carbodiimide hydrochloride (1.2 g) was added to the solution. To the resulting solution, a solution comprising L-norleucine methyl ester hydrochloride (1.8 g) and triethylamine (1.2 g) dissolved in dry methylene chloride (50 ml) was added and the mixture was stirred at room temperature for 12 hours. After completion of the reaction, the reaction solution was washed successivly with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-adamantyloxycarbonyl-L-leucyl-L-norleucine methyl ester (2.8 g, oil) was obtained.

(c) Preparation of N-adamantyloxycarbonyl-L-leucyl-L-norleucinol

N-adamantyloxycarbonyl-L-leucyl-L-norleucine methyl ester (2.6 g) prepared in step (b) and sodium borohydride (1.0 g) were suspended in t-butyl alcohol (50 ml) and the suspension was refluxed (90° C.) under nitrogen atmosphere. Absolute methanol (10 ml) was then added dropwise under reflux. After completion of the addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-adamantyloxycarbonyl-L-leucyl-L-norleucinol (2.2 g, powder) was obtained.

(d) Preparation of N-adamantyloxycarbonyl-L-leucyl-L-norleucinal

N-adamantyloxycarbonyl-L-leucyl-L-norleucinol (1.0 g) prepared in step (c) and triethylamine (1.0 g) were dissolved in anhydrous dimethyl sulfoxide (10 ml). To the resulting solution, a solution of sulfur trioxide-pyridine complex (1.6 g) in dimethyl sulfoxide (12 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was purified by reverse-phase medium-pressure column chromatography using octadecyl silane, whereupon N-adamantyloxycarbonyl-L-leucyl-L-norleucinal (0.8 g, powder) was obtained as the end compound.

EXAMPLE 6

Production of N-(p-chlorobenzyloxycarbonyl)-L-leucyl-L-norleucinal [compound of formula (1) where $R_1=(4-Cl)C_6H_4CH_2OCO-$, $R_2=H-$, $R_3=(CH_3)_2CHCH_2-$, and $R_4=CH_3(CH_2)_3-$]

(a) Preparation of N-(p-chlorobenzyloxycarbonyl)-L-leucine dicyclohexylamine salt L-leucine (3.9 g) and potassium carbonate (4.2 g) were dissolved in water (100 ml). To the ice-cooled solution, a solution of (p-chloro)benzyloxycarbonyl chloride (6.2 g) in dioxane (10 ml) was added and the mixture was stirred at room temperature for 8 hours. After completion of the reaction, the reaction solution was washed with ether and 5N HCl was added to the aqueous phase to lower the pH to 2 or below and extraction was conducted with ethyl acetate. The extract was dried over anhydrous sodium sulfate and the solvent was concentrated under reduced pressure. When dicyclohexylamine (6.0 ml) was added to the solution, the titled N-(p-chlorobenzyloxycarbonyl)-L-leucine dicyclohexylamine salt (9.5 g, crystal) was obtained.

(b) Preparation of N-(p-chlorobenzyloxycarbonyl)-L-leucyl-L-norleucine methyl ester N-(p-chlorobenzyloxycarbonyl)-L-leucine dicyclohexylamine salt (4.8 g) prepared in step (a) was suspended in ethyl acetate (100 ml). After washing the suspension with a 10% aqueous solution of citric acid, the organic layer was dried over sodium sulfate. The solvent was distilled off under reduced pressure and the residue was dissolved in dry methylene chloride (50 ml). To the solution, 1-ethyl-3-(3-dimethylaminopropyl)carbodiimide hydrochloride (2.2 g) was added. To the resulting solution was added a solution of L-norleucine methyl ester hydrochloride (1.8 g) and triethylamine (1.2 g) dissolved in dry methylene chloride (50 ml) and the mixture was stirred at room temperature for 12 hours. After completion of the reaction, the reaction solution was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-(p-chlorobenzyloxycarbonyl)-L-leucyl-L-norleucine methyl ester (3.0 g, crystal) was obtained.

(c) Preparation of N-(p-chlorobenzyloxycarbonyl)-L-leucyl-L-norleucinol

N-(p-chlorobenzyloxycarbonyl)-L-leucyl-L-norleucine methyl ester (3.0 g) prepared in step (b) and sodium borohydride (1.0 g) were suspended in t-butyl alcohol (40 ml) and the suspension was refluxed (90° C.) under nitrogen atmosphere. Absolute methanol (10 ml) was then added dropwise under reflux. After completion of the dropwise addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-(p-chlorobenzyloxycarbonyl)-L-leucyl-L-norleucinol (2.2 g, oil) was obtained.

(d) Preparation of N-(p-chlorobenzyloxycarbonyl)-L-leucyl-L-norleucinal

N-(p-chlorobenzyloxycarbonyl)-L-leucyl-L-norleucinol (1.0 g) prepared in step (c) and triethylamine (1.2 g) were dissolved in anhydrous dimethyl sulfoxide (10 ml). To the resulting solution, a solution of sulfur trioxide-pyridine complex (2.0 g) in dimethyl sulfoxide (10 ml) was added. After being stirred at room temperature for 10 minutes, the mixture was poured into ice water (200 ml), followed by extractions with ethyl acetate three times, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-(p-chlorobenzyloxycarbonyl)-L-leucyl-L-norleucinal (0.7 g, crystal) was obtained as the end compound.

EXAMPLE 7

Production of N-(p-methoxybenzyloxycarbonyl)-L-leucyl-L-norleucinal [compound of formula (I) where $R_1=(4-CH_3O)C_6H_4CH_2OCO-$, $R_2=H-$, $R_3=(CH_3)_2CHCH_2-$, and $R_4=CH_3(CH_2)_3-$]

(a) Preparation of N-(p-methoxybenzyloxycarbonyl)-L-leucine dicyclohexylammonium salt L-leucine (3.9 g) and triethylamine (7.0 g) were dissolved in water (15 ml). To the ice-cooled solution, a solution of p-methoxybenzyl-s-4,6-dimethylpyrimidine-2-ylthiocarbonate (9.1 g) in dioxane (20 ml) was added and the mixture was stirred at room temperature for 5 hours. After completion of the reaction, 150 ml of water was added to the reaction solution and the mixture was washed with ethyl acetate. 5N HCl was added to the aqueous phase to lower the pH to 2 or below and extraction was conducted with ethyl acetate. The extract was dried over anhydrous sodium sulfate and the solvent was concentrated under reduced pressure. When dicyclohexylamine (6.0 g) was added to the solution, the titled N-(p-methoxybenzyloxycarbonyl)-L-leucine dicyclohexylammonium salt (9.0 g, crystal) was obtained.

(b) Preparation of N-(p-methoxybenzyloxycarbonyl)-L-leucyl-L-norleucine methyl ester N-(p-methoxybenzyloxycarbonyl)-L-leucine dicyclohexylammonium salt (4.7 g) prepared in step (a) was suspended in ethyl acetate (100 ml). After washing the suspension with a 10% aqueous solution of citric acid, the organic layer was dried over sodium sulfate. The solvent was distilled off under reduced pressure and the residue was dissolved in dry methylene chloride (50 ml). To the solution, 1-ethyl-3-(3-dimethylaminopropyl)carbodiimide hydrochloride (2.2 g) was added. To the resulting solution was added a solution having L-norleucine methyl ester hydrochloride (1.8 g) and triethylamine (1.2 g) dissolved in dry methylene chloride (50 ml) and the mixture was stirred at room temperature for 12 hours. After completion of the reaction, the reaction solution was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-(p-methoxybenzyloxycarbonyl)-L-leucyl-L-norleucine methyl ester (3.0 g, crystal) was obtained.

(c) Preparation of N-(p-methoxybenzyloxycarbonyl)-L-leucyl-L-norleucinol

N-(p-methoxybenzyloxycarbonyl)-L-leucyl-L-norleucine methyl ester (2.0 g) prepared in step (b) and sodium borohydride (1.0 g) were suspended in t-butyl alcohol (40 ml) and the suspension was refluxed (90° C.) under nitrogen atmosphere. Absolute methanol (10 ml) was then added dropwise under reflux. After completion of the dropwise addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-(p-methoxybenzyloxycarbonyl)-L-leucyl-L-norleucinol (2.0 g, crystal) was obtained.

(d) Preparation of N-(p-methoxybenzyloxycarbonyl)-L-leucyl-L-norleucinal

N-(p-methoxybenzyloxycarbonyl)-L-leucyl-L-norleucinol (1.0 g) prepared in step (c) and triethylamine (1.2 g) were dissolved in anhydrous dimethyl sulfoxide (10 ml). To the resulting solution, a solution of sulfur trioxide-pyridine complex (2.0 g) in dimethyl sulfoxide (10 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-(p-methoxybenzyloxycarbonyl)-L-leucyl-L-norleucinal (0.7 g, crystal) was obtained as the end compound.

EXAMPLE 8

Production of N-(p-nitrobenzyloxycarbonyl)-L-leucyl-L-norleucinal [compound of formula (1) where
$R_1 = (4-NO_2)C_6H_4CH_2OCO-$, $R_2 = H-$,
$R_3 = (CH_3)_2CHCH_2-$, and $R_4 = CH_3(CH_2)_3-$]

(a) Preparation of N-benzyloxycarbonyl-L-leucyl-L-norleucine methyl ester

N-benzyloxycarbonyl-L-leucine (7.4 g) was dissolved in dry methylene chloride (100 ml). To the solution, 1-ethyl-3-(3-dimethylaminopropyl)carbodiimide hydrochloride (8.2 g) was added. To the resulting solution was added a solution having L-norleucine methyl ester hydrochloride (7.4 g) and triethylamine (4.2 g) dissolved in dry methylene chloride (100 ml) and the mixture was stirred at room temperature for 12 hours. After completion of the reaction, the reaction solution was washed successively with 1N HCl, brine, saturated sodium hydrogencarbonate and brine, followed by drying over anhydrous sodium sulfate. Thereafter, the solvent was distilled off under reduced pressure. When the residue was purified by medium-pressure column chromatography using silica gel, the titled N-benzyloxycarbonyl-L-leucyl-L-norleucine methyl ester (12 g, crystal) was obtained.

(b) Preparation of N-benzyloxycarbonyl-L-leucyl-L-norleucinol

N-benzyloxycarbonyl-L-leucyl-L-norleucine methyl ester (10 g) prepared in step (b) and sodium borohydride (3.0 g) were suspended in t-butyl alcohol (100 ml) and the suspension was refluxed (90° C.) under nitrogen atmosphere. Absolute methanol (20 ml) was then added dropwise under reflux. After completion of the dropwise addition, the mixture was stirred under reflux for 30 minutes and restored to room temperature, followed by addition of water (100 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-benzyloxycarbonyl-L-leucyl-L-norleucinol (8.0 g, crystal) was obtained.

(c) Preparation of N-(p-nitrobenzyloxycarbonyl)-L-leucyl-L-norleucinol

N-benzyloxycarbonyl-L-leucyl-L-norleucinol (2.5 g) prepared in step (b) was dissolved in ethanol (50 ml) and, following the addition of a catalytic amount of palladium on carbon, the reaction solution was stirred for 3 hours under hydrogen atmosphere. After completion of the reaction, the catalyst was separated by filtration. When the solvent was distilled off from the filtrate under reduced pressure, L-leucyl-L-norleucinol was obtained quantitatively. To the product, water (20 ml) and sodium hydrogencarbonate (1.5 g) were added, and following the addition of a solution of p-nitrobenzyloxycarbonyl chloride (1.5 g) in ether (10 ml), the mixture was stirred at room temperature for 3 hours. After completion of the reaction, extraction was conducted three times with ethyl acetate. The extracts were combined, washed with brine and dried over anhydrous magnesium sulfate. After distilling off ethyl acetate under reduced pressure, the residue was subjected to recrystallization from a mixed solvent of ethyl acetate and hexane, whereupon the titled N-(p-nitrobenzyloxycarbonyl)-L-leucyl-L-norleucinol (2.0 g, crystal) was obtained.

(d) Preparation of N-(p-nitrobenzyloxycarbonyl)-L-leucyl-L-norleucinal

N-(p-nitrobenzyloxycarbonyl)-L-leucyl-L-norleucinol (1.0 g) prepared in step (c) and triethylamine (1.2 g) were dissolved in anhydrous dimethyl sulfoxide (10 ml). To the resulting solution, a solution of sulfur trioxide-pyridine complex (2.0 g) in dimethyl sulfoxide (10 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-(p-nitrobenzyloxycarbonyl)-L-leucyl-L-norleucinal (0.8 g, crystal) was obtained as the end compound.

EXAMPLE 9

Production of N-(o-chlorobenzyloxycarbonyl)-L-leucyl-L-norleucinal [compound of formula (1) where $R_1=(2-Cl)C_6H_4CH_2OCO-$, $R_2=H-$, $R_3=(CH_3)_2CHCH_2-$, and $R_4=CH_3(CH_2)_3-$]

(a) Preparation of N-(o-chlorobenzyloxycarbonyl)-L-leucine dicyclohexylammonium salt L-leucine ethyl ester hydrochloride (4.0 g) and triethylamine (2.1 g) were dissolved in dry tetrahydrofuran (100 ml). To the ice-cooled solution, N-(2-chlorobenzyloxycarbonyl)oxysuccinimide (5.0 g) was added and the mixture was stirred at room temperature for 12 hours. After completion of the reaction, the solvent was distilled off under reduced pressure and, following the addition of water (50 ml), extraction was conducted with ethyl acetate. The extract was dried over anhydrous sodium sulfate and the solvent was distilled off under reduced pressure. When the residue was purified by medium-pressure column chromatography using silica gel, N-(o-chlorobenzyloxycarbonyl)-L-leucine ethyl ester (7.0 g, oil) was obtained.

This compound was dissolved in methanol (20 ml). To the solution, 1N aqueous sodium hydroxide (30 ml) and water (50 ml) were added and the mixture was stirred with heating at 80° C. for 1 hour. After completion of the reaction, the reaction solution was washed with ethyl acetate and 5N HCl was added to the aqueous phase to lower the pH to 2 or below and extraction was conducted with ethyl acetate. The extract was dried over anhydrous sodium sulfate and concentrated under reduced pressure. When dicyclohexylamine (6.0 g) was added, the titled N-(o-chlorobenzyloxycarbonyl)-L-leucine dicyclohexylamine salt (5.5 g, crystal) was obtained.

(b) Preparation of N-(o-chlorobenzyloxycarbonyl)-L-leucyl-L-norleucine methyl ester N-(o-chlorobenzyloxycarbonyl)-L-leucine dicyclohexylammonium salt (4.8) prepared in step (a) was suspended in ethyl acetate (100 ml). After washing the suspension with a 10% aqueous solution of citric acid, the organic layer was dried over anhydrous sodium sulfate. The solvent was distilled off under reduced pressure and the residue was dissolved in dry methylene chloride (50 ml). To the solution, 1-ethyl-3-(3-dimethylaminopropyl)carbodiimide hydrochloride (2.2 g) was added. To the resulting solution was added a solution having L-norleucine methyl ester hydrochloride (1.8 g) and triethylamine (1.2 g) dissolved in dry methylene chloride (50 ml) and the mixture was stirred at room temperature for 12 hours. After completetion of the reaction, the reaction solution was washed successively with 1N HCl, brine, saturated sodium hydrogencarbonate, and brine, followed by drying over sodium sulfate. Thereafter, the solvent was distilled off under reduced pressure. When the residue was purified by medium-pressure column chromatography using silica gel, the titled N-(o-chlorobenzyloxycarbonyl)-L-leucyl-L-norleucine methyl ester (3.0 g, crystal) was obtained.

(c) Preparation of N-(o-chlorobenzyloxycarbonyl)-L-leucyl-L-norleucinol

N-(o-chlorobenzyloxycarbonyl)-L-leucyl-L-norleucine methyl ester (3.0 g) prepared in step (b) and sodium borohydride (1.0 g) were suspended in t-butyl alcohol (50 ml) and the suspension was refluxed (90° C.) under nitrogen atmosphere. Absolute methanol (10 ml) was then added dropwise under reflux. After completion of the dropwise addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-(o-chlorobenzyloxycarbonyl)-L-leucyl-L-norleucinol (2.0 g, crystal) was obtained.

(d) Preparation of N-(o-chlorobenzyloxycarbonyl)-L-leucyl-L-norleucinal

N-(o-chlorobenzyloxycarbonyl)-L-leucyl-L-norleucinol (1.0 g) prepared in step (c) and triethylamine (1.2 g) were dissolved in anhydrous dimethyl sulfoxide (15 ml). To the resulting solution, a solution of sulfur trioxide-pyridine complex (2.0 g) in dimethyl sulfoxide (15 ml) was added. After being stirred at room temperature for 10 minutes, the mixture was poured into ice water (200 ml), followed by three extractions with ethyl acetate, successive washing with 10% aqueous citric acid, brine, saturated sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-(o-chlorobenzyloxycarbonyl)-L-leucyl-L-norleucinal (0.8 g, crystal) was obtained as the end compound.

EXAMPLE 10

Production of N-(2,2,2-trichloro)ethyloxycarbonyl-L-leucyl-L-norleucinal [compound of formula (1) where $R_1=CCl_3CH_2OCO-$, $R_2=H-$, $R_3=(CH_3)_2CHCH_2-$, and $R_4=CH_3(CH_2)_3-$]

(a) Preparation of N-benzyloxycarbonyl-L-leucyl-L-norleucine methyl ester

N-benzyloxycarbonyl-L-leucine (7.4 g) was dissolved in dry methylene chloride (100 ml). To the solution, 1-ethyl-3-(3-dimethylaminopropyl)carbodiimide hydrochloride (8.2 g) was added. To the resulting solution was added a solution having L-norleucine methyl ester hydrochloride (7.4 g) and triethylamine (4.2 g) dissolved in dry methylene chloride (100 ml) and the mixture was stirred at room temperature for 12 hours. After completion of the reaction, the reaction solution was washed successively with 1N HCl, brine, saturated sodium hydrogencarbonate, and brine, followed by drying over sodium sulfate. Thereafter, the solvent was distilled off under reduced pressure. When the residue was purified by medium-pressure column chromatography using silica gel, the titled N-benzyloxycarbonyl-L-leucyl-L-norleucine methyl ester (12 g, crystal) was obtained.

(b) Preparation of N-benzyloxycarbonyl-L-leucyl-L-norleucinol

N-benzyloxycarbonyl-L-leucyl-L-norleucine methyl ester (10 g) prepared in step (a) and sodium borohydride (3.0 g) were suspended in t-butyl alcohol (100 ml) and the suspension was refluxed (90° C.) under nitrogen atmosphere. Absolute methanol (20 ml) was then added dropwise under reflux. After completion of the dropwise addition, the mixture was stirred under reflux for 30 minutes and restored to room temperature, followed by addition of water (100 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-benzyloxycarbonyl-L-leucyl-L-norleucinol (8.0 g, crystal) was obtained.

(c) Preparation of N-(2,2,2-trichloroethyloxycarbonyl)-L-leucyl-L-norleucinol

N-benzyloxycarbonyl-L-leucyl-L-norleucinol (2.5 g) prepared in step (b) was dissolved in ethanol (50 ml) and, following the addition of a catalytic amount of palladium on carbon, the solution was stirred for 3 hours under hydrogen atmosphere. After completion of the reaction, the catalyst was separated by filtration. When the solvent was distilled off from the filtrate under reduced pressure, L-leucyl-L-norleucinol was obtained quantitatively. To the product, water (20 ml) and sodium hydrogencarbonate (2.2 g) were added, and following the addition of a solution of 2,2,2-trichloroethyloxycarbonyl chloride (1.5 g) in ether (10 ml), the mixture was stirred at room temperature for 12 hours. After completion of the reaction, extraction was conducted three times with ethyl acetate. The extracts were combined, washed with brine and dried over anhydrous magnesium sulfate. After distilling off ethyl acetate under reduced pressure, the residue was subjected to recrystallization from a mixed solvent of ethyl acetate and hexane, whereupon the titled N-(2,2,2-trichloroethyloxycarbonyl)-L-leucyl-L-norleucinol (1.0 g, crystal) was obtained.

(d) Preparation of N-(2,2,2-trichloroethyloxycarbonyl)-L-leucyl-L-norleucinal

N-(2,2,2-trichloroethyloxycarbonyl)-L-leucyl-L-norleucinol (0.7 g) prepared in step (c) and triethylamine (1.0 g) were dissolved in anhydrous dimethyl sulfoxide (10 ml). To the resulting solution, a solution of sulfur trioxide-pyridine complex (1.5 g) in dimethyl sulfoxide (10 ml) was added. After being stirred at room temperature for 10 minutes, the mixture was poured into ice water (200 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was subjected to recrystallization from a mixed solvent of ethyl acetate and hexane, whereupon N-2,2,2-trichloroethyloxycarbonyl)-L-leucyl-L-norleucinal (0.5 g, crystal) was obtained as the end compound.

EXAMPLE 11

Production of N-(2-trimethylsilylethyloxycarbonyl)-L-leucyl-L-norleucinal [compound of formula (1) where $R_1 = (CH_3)_3SiCH_2CH_2$—OCO—, $R_2 = H$-, $R_3 = (CH_3)_2CHCH_2$—, and $R_4 = CH_3(CH_2)_3$—]

(a) Preparation of p-nitrophenyltrimethylsilylethyloxycarboxylate

Trimethylsilyl ethanol (4.4 g) and bis(p-nitrophenyl) carbonate (10 g) were dissolved in dry methylene chloride (100 ml). To the resulting solution, N-methylmorpholine (6.0 g) was added and the mixture was stirred at room temperature for 12 hours. After completion of the reaction, the reaction solution was washed successively with 0.1% sulfuric acid, brine, saturated sodium hydrogencarbonate and brine, and dried over anhydrous sodium sulfate. After distilling off ethyl acetate under reduced pressure, the residue was purified by medium pressure column chromatography using silica gel, whereupon the titled p-nitrophenyltrimethylsilylethyloxycarboxylate (5.0 g, crystal) was obtained.

(b) Preparation of N-(2-trimethylsilyl)ethyloxycarbonyl-L-leucine dicyclohexyl ammonium salt L-leucine methyl ester hydrochloride (4.0 g) and triethylamine (2.2 g) were dissolved in dry dimethylformamide (100 ml), and p-nitrophenyltrimethylsilylethyloxycarboxylate (5.8 g) was added to the solution. To the resulting solution, 1-hydroxybenzotriazole monohydrate (200 mg) was added as a catalyst and the mixture was stirred at room temperature for 12 hours. After completion of the reaction, the reaction solution was concentrated under reduced pressure and, following addition of water, extraction with ethyl acetate was performed. The extract was washed successively with 10% aqueous citric acid, brine, saturated aqueous anhydrous sodium hydrogencarbonate and brine. After drying over anhydrous sodium sulfate, the solvent was distilled off under reduced pressure and the residue was purified by medium-pressure column chromatography using silica gel, whereupon the titled N-(2-trimethylsilyl)ethyloxycarbonyl-L-leucine ethyl ester (7.0 g, crystal) was obtained. The ester was dissolved in methanol (20 ml), and following the addition of 1N aqueous NaOH (30 ml) and water (50 ml), the mixture was stirred at 80° C. for 1 hour. After completion of the reaction, the reaction solution was washed with ethyl acetate and 0.1% sulfuric acid was added to the aqueous phase to lower the pH to 2 or below and extraction was conducted with ethyl acetate. The extract was dried over anhydrous sodium sulfate and concentrated under reduced pressure. Upon addition of dicyclohexylamine (6.0 g), the titled N-(2-trimethylsilyl)ethyloxycarbonyl-L-leucine dicyclohexyl ammonium salt (5.5 g, crystal) was obtained.

(c) Preparation of N-(2-trimethylsilyl)ethyloxycarbonyl-L-leucyl-norleucine methyl ester N-(2-trimethylsilyl)ethyloxycarbonyl-L-leucine dicyclohexyl ammonium salt (4.6 g) prepared in step (b) was suspended in ethyl acetate (100 ml). After washing the suspension with a 10% aqueous solution of citric acid, the organic layer was dried over anhydrous sodium sulfate. The solvent was distilled off under reduced pressure and the resulting N-(2-trimethylsilyl)ethyloxycarbonyl-L-leucine was dissolved in dry methylene chloride (50 ml). To the solution, 1-ethyl-3-(3-dimethylaminopropyl)carbodiimide hydrochloride (2.0 g) was added. To the resulting solution was added a solution of L-norleucine methyl ester hydrochloride (1.8 g) and triethylamine (1.2 g) dissolved in dry methylene chloride (50 ml) and the mixture was stirred at room temperature for 12 hours. After completion of the reaction, the reaction solution was washed successively with 10% citric acid, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, the titled N-(2-trimethylsilyl)ethyloxycarbonyl-L-leucyl-norleucine methyl ester (2.8 g, oil) was obtained.

(d) Preparation of N-(2-trimethylsiyl)ethyloxycarbonyl-L-leucyl-L-norleucinol

N-(2-trimethylsilyl)ethyloxycarbonyl-L-leucyl-norleucine methyl ester (2.8 g) prepared in step (c) and sodium borohydride (1.5 g) were suspended in t-butyl alcohol (40 ml) and the suspension was refluxed (90° C.) under nitrogen atmosphere. Absolute methanol (12 ml) was then added dropwise under reflux. After completion of the addition, the mixture was stirred under reflux for 30 minutes and restored to room temperature, followed by addition of water (30 ml) with ice cooling. After distilling off methanol and t-butyl alcohol under reduced pressure, the residue was extracted three times with ethyl acetate. The extracts were combined, washed with brine and dried over anhydrous magnesium sulfate. After distilling off ethyl acetate under reduced pressure, the residue was purified by medium-pressure column chromatography using silica gel, whereupon the titled N-(2-trimethylsilyl)ethyloxycarbonyl-L-leucyl-L-norleucinol (2.0 g, crystal) was obtained.

(e) Preparation of N-(2-trimethylsilyl)ethyloxycarbonyl-L-leucyl-L-norleucinal

N-(2-trimethylsilyl)ethyloxycarbonyl-L-leucyl-L-norleucinol (1.8 g) prepared in step (d) and triethylamine (1.9 g) were dissolved in anhydrous dimethyl sulfoxide (20 ml). To the resulting solution, a solution of sulfur trioxide-pyridine complex (3.0 g) in dimethyl sulfoxide (20 ml) was added. After being stirred at room temperature for 20 minutes, the mixture was poured into ice water (300 ml), followed by three extractions with ethyl acetate, successive washing with 10% aqueous citric acid, brine, saturated aqueous sodium hydrogencarbonate and brine, and drying over anhydrous sodium sulfate. After distilling off ethyl acetate under reduced pressure, the residue was purified by reverse-phase medium-pressure column chromatography using an octadecyl silane, whereupon N-(2-trimethylsilyl)ethyloxycarbonyl-L-leucyl-L-norleucinal (1.0 g, oil) was obtained as the end compound.

EXAMPLE 12

Production of N-(p-toluenesulfonyl)-L-leucyl-L-norleucinal [compound of formula (1) where $R_1=(4-CH_3)C_6H_4SO_2-$, $R_2=H-$, $R_3=(CH_3)_2CHCH_2-$, $R_4=CH_3(CH_2)_3-$]

(a) Preparation of N-(p-toluenesulfonyl)-L-leucine

L-leucine (2.6 ml) was dissolved in 2N NaOH (40 ml). To the ice-cooled solution, p-toluenesulfonyl chloride (3.8 g) was added and the mixture was stirred at room temperature for 8 hours. After completion of the reaction, the reaction solution was washed with ethyl acetate and 5N HCl was added to the aqueous phase to lower the pH to 2 or below and extraction was conducted with ethyl acetate. The extract was dried over anhydrous sodium sulfate and the solvent was distilled off under reduced pressure. When the residue was subjected to recrystallization from a mixed solvent of ethyl acetate and hexane, the titled N-(p-toluenesulfonyl)-L-leucine (3.6 g, crystal) was obtained.

(b) Preparation of N-(p-toluenesulfonyl)-L-leucyl-L-norleucine methyl ester

N-(p-toluenesulfonyl)-L-leucine (1.8 g) prepared in step (a) was dissolved in dry methylene chloride (50 ml) and 1-ethyl-3-(3-dimethylaminopropyl)carbodiimide hydrochloride (1.2 g) was added. To this solution, a solution of L-norleucine methyl ester hydrochloride (1.8 g) and triethylamine (1.2 g) in dry methylene chloride (50 ml) was added, and the mixture was stirred at room temperature for 12 hours. After completion of the reaction, the product was washed successively with 1N HCl, brine, saturated sodium hydrogencarbonate, and brine, followed by drying over anhydrous sodium sulfate. The solvent was distilled off under reduced pressure. When the product was purified by medium-pressure column chromatography using silica gel, the titled N-(p-toluenesulfonyl)-L-leucyl-L-norleucine methyl ester (2.8 g, oil) was obtained.

(c) Preparation of N-(p-toluenesulfonyl)-L-leucyl-L-norleucinol

N-(p-toluenesulfonyl)-L-leucyl-L-norleucine methyl ester (2.8 g) prepared in step (b) and sodium borohydride (1.5 g) were suspended in t-butyl alcohol (40 ml) which was then refluxed (90° C.) under nitrogen atmosphere. Absolute methanol (12 ml) was then added dropwise under reflux. After the addition, the stirring was continued for 30 minutes under reflux. After the mixture was restored to room temperature, water (30 ml) was added thereto with ice cooling. The methanol and t-butyl alcohol were distilled off under reduced pressure. The residue was extracted with ethyl acetate 3 times, washed with brine and dried over anhydrous magnesium sulfate. When ethyl acetate was distilled off and the residue was purified by medium-pressure column chromatography using silica gel, the titled N-(p- toluenesulfonyl)-L-leucyl-L-norleucinol (2.0 g, crystal) was obtained.

(d) Preparation of
N-(p-toluenesulfonyl)-L-leucyl-L-norleucinal

N-(p-toluenesulfonyl)-L-leucyl-L-norleucinol (1.0 g) prepared in step (c) and triethylamine (1.2 g) were dissolved in anhydrous dimethyl sulfoxide (12 ml). A solution of sulfur trioxide-pyridine complex (2.0 g) in dimethyl sulfoxide (12 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over anhydrous sodium sulfate. Ethyl acetate was distilled off under reduced pressure. When the residue was subjected to recrystallization from a mixed solvent of ethyl acetate and hexane, the titled N-(p-toluenesulfonyl)-L-leucyl-L-norleucinal (0.7 g, crystal) was obtained.

EXAMPLE 13

Production of
N-(o-nitro)phenylsulfenyl-L-leucyl-L-norleucinal
[compound of formula (1) where
$R_1=(2-NO_2)C_6H_4S-$, $R_2=H-$,
$R_3=(CH_3)_2CHCH_2-$, $R_4=CH_3(CH_2)_3-$]

(a) Preparation of N-(o-nitrophenylsulfenyl)-L-leucine dicyclohexylamine salt

L-leucine (5.0 g) and (o-nitro)phenylsulfenyl chloride (8.0 g) were dissolved in 2N NaOH (25 ml). 1,4-dioxane (25 ml) was added thereto and the mixture was stirred at room temperature for 1 hour. After completion of the reaction and addition of 2N $H_2SO_4$, the mixture was extracted with ether. The extract was dried over anhydrous sodium sulfate, the solvent was concentrated under reduced pressure. When dicyclohexylamine (8.0 g) was added, the titled N-(o-nitrophenylsulfenyl)-L-leucine dicyclohexyl ammonium salt (10 g, crystal) was obtained.

(b) Preparation of
N-(o-nitro)phenylsulfenyl-L-leucyl-L-norleucine methyl ester

N-(o-Nitro)phenylsulfenyl-L-leucine dicyclohexyl ammonium salt (4.6 g) was suspended in ethyl acetate (100 ml). After washing the suspension with 10% citric acid, the organic layer was dried over anhydrous sodium sulfate. The solvent was distilled off under reduced pressure and the residue was dissolved in dry methylene chloride (50 ml). To the solution, 1-ethyl-3-(3-dimethylaminopropyl)carbodiimide hydrochloride (2.0 g) was added. To the resulting solution was added a solution of L-norleucine methyl ester hydrochloride (1.8 g) and triethylamine (1.0 g) in dry methylene chloride (50 ml) and the mixture was stirred at room temperature for 12 hours. After completion of the reaction, the mixture was washed with 10% citric acid, brine, saturated sodium hydrogencarbonate, and brine, followed by drying over anhydrous sodium sulfate. The solvent was distilled off under reduced pressure. When the residue was purified by medium-pressure column chromatography using silica gel, the titled N-(o-nitrophenylsulfenyl)-L-leucyl-L-norleucine methyl ester (5.0 g, oil) was obtained.

(c) Preparation of
N-(o-nitrophenylsulfenyl)-L-leucyl-L-norleucinol

N-(o-nitrophenylsulfenyl)-L-leucyl-L-norleucine methyl ester (3.2 g) prepared in step (b) and sodium borohydride (2.0 g) were suspended in t-butyl alcohol (50 ml) which was then refluxed (90° C.) under nitrogen atmosphere. Absolute methanol (15 ml) was then added dropwise under reflux. After the addition, the stirring was continued for 30 minutes under reflux. After the mixture was restored to room temperature, water (50 ml) was added thereto with ice cooling. The methanol and t-butyl alcohol were distilled off under reduced pressure. The residue was extracted with ethyl acetate 3 times, washed with brine and dried over anhydrous magnesium sulfate. When ethyl acetate was distilled off and the residue was purified by medium-pressure column chromatography using silica gel, the titled N-(o-nitrophenylsulfenyl)-L-leucyl-L-norleucinol (2.0 g, crystal) was obtained.

(d) Preparation of
N-(o-nitrophenylsulfenyl)-L-leucyl-L-norleucinal

N-(o-nitrophenylsulfenyl)-L-leucyl-L-norleucinol (1.0 g) prepared in step (c) and triethylamine (1.2 g) were dissolved in anhydrous dimethyl sulfoxide (12 ml). A solution of sulfur trioxide-pyridine complex (2.0 g) in dimethyl sulfoxide (12 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over anhydrous sodium sulfate. Ethyl acetate was distilled off under reduced pressure. When the residue was purified by medium-pressure reverse phase column chromatography using octadecyl silane, the titled N-(o-nitrophenylsulfenyl)-L-leucyl-L-norleucinal (1.2 g, oil) was obtained.

EXAMPLE 14

Production of
N-diphenylphosphonothioyl-L-leucyl-L-norleucinal
[compound of formula (1) where $R_1=(C_6H_5)_2PS-$,
$R_2=H-$, $R_3=(CH_3)_2CHCH_2-$, $R_4=CH_3(CH_2)_3-$]

(a) Preparation of
N-diphenylphosphonothioyl-L-leucyl-L-norleucine methyl ester

N-diphenylphosphonothioyl-L-leucine (2.0 g) was dissolved in dry methylene chloride (50 ml) and 1-ethyl-3-(3-dimethylaminopropyl)carbodiimide hydrochloride (2.0 g) was added. To this solution, a solution of L-norleucine methyl ester hydrochloride (1.8 g) and triethylamine (1.0 g) in dry methylene chloride (50 ml) was added, and the mixture was stirred at room temperature for 12 hours. After completion of the reaction, the product was washed successively with 10% citric acid, brine, saturated sodium hydrogencarbonate, and brine, followed by drying over anhydrous sodium sulfate. The solvent was distilled off under reduced pressure. When the residue was purified by medium-pressure column chromatography using silica gel, the titled N-diphenylphosphonothioyl-L-leucyl-L-norleucine methyl ester (3.0 g, oil) was obtained.

(b) Preparation of N-diphenylphosphonothioyl-L-leucyl-L-norleucinol

N-diphenylphosphonothioyl-L-leucyl-L-norleucine methyl ester (2.5 g) prepared in step (a) and sodium borohydride (1.0 g) were suspended in t-butyl alcohol (50 ml) which was then refluxed (90° C.) under nitrogen atmosphere. Absolute methanol (10 ml) was then added dropwise under reflux. After the addition, the stirring was continued for 30 minutes under reflux. After the mixture was restored to room temperature, water (50 ml) was added thereto with ice cooling. Methanol and t-butyl alcohol were distilled off under reduced pressure. The residue was extracted with ethyl acetate 3 times, washed with brine and dried over anhydrous magnesium sulfate. When ethyl acetate was distilled off and the residue was purified by medium-pressure column chromatography using silica gel, the titled N-diphenylphosphonothioyl-L-leucyl-L-norleucinol (2.0 g, crystal) was obtained.

(c) Preparation of N-diphenylphosphonothioyl-L-leucyl-L-norleucinal

N-diphenylphosphonothioyl-L-leucyl-L-norleucinol (1.0 g) prepared in step (b) and triethylamine (0.8 g) were dissolved in anhydrous dimethyl sulfoxide (8 ml). A solution of sulfur trioxide-pyridine complex (1.3 g) in dimethyl sulfoxide (8 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over anhydrous sodium sulfate. Ethyl acetate was distilled off under reduced pressure. When the residue was purified by medium-pressure reverse phase column chromatography using octadecyl silane, the titled N-diphenylphosphonothioyl-L-leucyl-L-norleucinal (0.6 g, oil) was obtained.

EXAMPLE 15

Production of N-triphenylmethyl-L-leucyl-L-norleucinal [compound of formula (1) where $R_1=(C_6H_5)_3C-$, $R_2=H-$, $R_3=(CH_3)_2CHCH_2-$, $R_4=CH_3(CH_2)_3-$]

(a) Preparation of N-benzyloxycarbonyl-L-leucyl-L-norleucine methyl ester

N-benzyloxycarbonyl-L-leucine (7.4 g) was dissolved in dry methylene chloride (100 ml). To the solution, 1-ethyl-3-(3-dimethylaminopropyl)carbodiimide hydrochloride (8.2 g) was added. To the resulting solution was added a solution of L-norleucine methyl ester hydrochloride (7.4 g) and triethylamine (4.2 g) in dry methylene chloride (100 ml) was then added and the mixture was stirred at room temperature for 12 hours. After the completion of the reaction, the mixture was washed with 1N HCl, brine, saturated sodium hydrogencarbonate, and brine, followed by drying over anhydrous sodium sulfate. The solvent was distilled off under reduced pressure. When the residue was purified by medium-pressure column chromatography using silica gel, the titled N-benzyloxycarbonyl-L-leucyl-L-norleucine methyl ester (12 g, crystal) was obtained.

(b) Preparation of N-triphenylmethyl-L-leucyl-L-norleucine methyl ester

N-benzyloxycarbonyl-L-leucyl-L-norleucine methyl ester (4.0 g) prepared in step (a) was dissolved in ethyl alcohol (50 ml) and a catalytic amount of paradium on carbon was added thereto. The mixture was stirred at room temperature for 3 hours under a hydrogen atmosphere. After the completion of the reaction the catalyst was filtered off and the solvent was distilled off under reduced pressure to give a quntitative amount of L-leucyl-L-norleucine methyl ester, which was then dissolved in dry methylene chloride (100 ml). To this solution, triethylamine (1.5 g) and triphenylmethane chloride (4.2 g) were added and the mixture was stirred at room temperature for 12 hours. After completion of the reaction, the mixture was washed with 10% citric acid, brine, saturated sodium hydrogencarbonate, and brine, followed by drying over sodium sulfate. The solvent was distilled off under reduced pressure. When the residue was purified by medium-pressure column chromatography using silica gel, the titled N-triphenylmethyl-L-leucyl-L-norleucine methyl ester (4.3 g, crystal) was obtained.

(c) Preparation of N-triphenylmethyl-L-leucyl-L-norleucinol

N-triphenylmethyl-L-leucyl-L-norleucine methyl ester (4.3 g) prepared in step (b) and sodium borohydride (1.5 g) were suspended in t-butyl alcohol (50 ml) which was then refluxed (90° C.) under nitrogen atmosphere. Absolute methanol (15 ml) was then added dropwise under reflux. After the addition, the stirring was continued for 30 minutes under reflux. After the mixture was restored to room temperature, water (100 ml) was added thereto with ice cooling. Methanol and t-butyl alcohol were distilled off under reduced pressure. The residue was extracted with ethyl acetate 3 times, washed with brine and dried over anhydrous magnesium sulfate. Then ethyl acetate was distilled off and the residue was purified by medium-pressure column chromatography using silica gel, the titled N-triphenylmethyl-L-leucyl-L-norleucinol (2.8 g, powdery crystal) was obtained.

(d) Preparation of N-triphenylmethyl-L-leucyl-L-norleucinal

N-triphenylmethyl-L-leucyl-L-norleucinol (1.0 g) prepared in step (c) and triethylamine (2.1 g) were dissolved in anhydrous dimethyl sulfoxide (10 ml). A solution of sulfur trioxide-pyridine complex (2.0 g) in dimethyl sulfoxide (10 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over anhydrous sodium sulfate. Ethyl acetate was distilled off under reduced pressure. When the residue was recrystallized from a mixed solvent of ethyl acetate and hexane, the titled N-triphenylmethyl-L-leucyl-L-norleucinal (0.7 g, crystal) was obtained.

EXAMPLE 16

Production of
N-(2-benzoyl-1-methylvinyl)-L-leucyl-L-norleucinal
[compound of formula (1) where
$R_1 = C_6H_5COCH=C(CH_3)-$, $R_2 = H-$,
$R_3 = (CH_3)_2CHCH_2-$, $R_4 = CH_3(CH_2)_3-$]

(a) Preparation of
N-(2-benzoyl-1-methylvinyl-L-leucine

Benzoyl acetone (6.6 g) was dissolved in dry ethanol (100 ml). To this solution was added a solution of NaOH (1.8 g) in dry methanol (20 ml). L-leucine (5.4 g) was further added and the mixture was refluxed (100° C.) for 3 hours. After completion of the reaction, the solvent was distilled off under reduced pressure, water was added to the residue and the pH value was lowered to about 2 with 10% citric acid. The product was extracted with ether, the extract was dried over sodium sulfate and the solvent was distilled off under reduced pressure. After recrystallization of the residue in a mixed solvent of ethyl acetate and hexane, the titled N-(2-benzoyl-1-methylvinyl)-L-leucine (7.0 g, crystal) was obtained.

(b) Preparation of
N-(2-benzoyl-1-methylvinyl)-L-leucyl-L-norleucine methyl ester N-(2-benzoyl-1-methyl)vinyl-L-leucine (2.8 g) prepared in step (a) was dissolved in dry methylene chloride (50 ml) and 1-ethyl-3-(3-dimethylaminopropyl)carbodiimide hydrochloride (2.0 g) was added. To this solution, a solution of L-norleucine methyl ester hydrochloride (1.8 g) and triethylamine (1.0 g) in dry methylene chloride (50 ml) was added, and the mixture was stirred at room temperature for 12 hours. After completion of the reaction, the product was washed successively with 10% citric acid, brine, saturated sodium hydrogencarbonate, and brine, followed by drying over sodium sulfate. The solvent was distilled off under reduced pressure. When the residue was purified by medium-pressure column chromatography using silica gel, the titled N-(2-benzoyl-1-methylvinyl)-L-leucyl-L-norleucine methyl ester (3.5 g, oil) was obtained.

(c) Preparation of
N-(2-benzoyl-1-methylvinyl)-L-leucyl-L-norleucinol

N-(2-benzoyl-1-methylvinyl)-L-leucyl-L-norleucine methyl ester (2.5 g) prepared in step (b) and sodium borohydride (1.0 g) were suspended in t-butyl alcohol (50 ml) which was then refluxed (90° C.) under nitrogen atmosphere. Absolute methanol (10 ml) was then added dropwise under reflux. After the addition, the stirring was continued for 30 minutes under reflux. After the mixture was restored to room temperature, water (50 ml) was added thereto with ice cooling. The methanol and t-butyl alcohol were distilled off under reduced pressure. The residue was extracted with ethyl acetate 3 times, washed with brine and dried over anhydrous magnesium sulfate. Then ethyl acetate was distilled off and the residue was purified by medium-pressure column chromatography using silica gel, the titled N-(2-benzoyl-1-methylvinyl)-L-leucyl-L-norleucinol (2.0 g, crystal) was obtained.

(d) Preparation of
N-(2-benzoyl-1-methylvinyl)-L-leucyl-L-norleucinal

N-(2-benzoyl-1-methylvinyl)-L-leucyl-L-norleucinol (1.0 g) prepared in step (c) and triethylamine (1.2 g) were dissolved in anhydrous dimethyl sulfoxide (12 ml). A solution of sulfur trioxide-pyridine complex (2.0 g) in dimethyl sulfoxide (12 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over sodium sulfate. Ethyl acetate was distilled off under reduced pressure. When the residue was purified by medium-pressure reverse phase column chromatography using octadecyl silane, the titled (-(2benzoyl-1-methylvinyl)-L-leucyl-L-norleucinal (0.6 g, oil) was obtained.

EXAMPLE 17

Production of N-phthaloyl-L-leucyl-L-norleucinal
[compound of formula (1) where $R_1$ and $R_2$ (these are taken together) = 1,2—(CO—)$_2$C$_6$H$_4$—,
$R_3 = (CH_3)_2CHCH_2-$, $R_4 = CH_3(CH_2)_3-$]

(a) Preparation of
N-benzyloxycarbonyl-L-leucyl-L-norleucine methyl ester

N-benzyloxycarbonyl-L-leucine (7.4 g) was dissolved in dry methylene chloride (100 ml). To the solution, 1-ethyl-3-(3-dimethylaminopropyl)carbodiimide hydrochloride (8.2 g) was added. To the resulting solution, a solution of L-norleucine methyl ester hydrochloride (7.4 g) and triethylamine (4.2 g) in dry methylene chloride (100 ml) was added and the mixture was stirred at room temperature for 12 hours. After completion of the reaction, the mixture was washed with 1N HCl, brine, saturated sodium hydrogencarbonate, and brine, followed by drying over sodium sulfate. The solvent was distilled off under reduced pressure. When the residue was purified by medium-pressure column chromatography using silica gel, the titled N-benzyloxycarbonyl-L-leucyl-L-norleucine methyl ester (12 g, crystal) was obtained.

(b) Preparation of
N-benzyloxycarbonyl-L-leucyl-L-norleucinol

N-benzyloxycarbonyl-L-leucyl-L-norleucine methyl ester (10 g) prepared in step (a) and sodium borohydride (3.0 g) were suspended in t-butyl alcohol (100 ml) and the suspension was refluxed (90° C.) under nitrogen atmosphere. Absolute methanol (20 ml) was then added dropwise under reflux. After completion of the dropwise addition, the mixture was stirred under reflux for 30 minutes and restored to room temperature, followed by addition of water (100 ml) with ice cooling. After distilling off methanol and t-butyl alcohol under reduced pressure, the residue was extracted three times with ethyl acetate. The extract was washed with brine and dried over anhydrous magnesium sulfate. After distilling off ethyl acetate under reduced pressure, the residue was purified by medium-pressure column chromatography using silica gel, whereupon the titled N-benzyloxycarbonyl-L-leucyl-L-norleucinol (8.0 g, crystal) was obtained.

(c) Preparation of N-phthaloyl-L-leucyl-L-norleucinol

N-benzyloxycarbonyl-L-leucyl-L-norleucinol (2.5 g) prepared in step (b) was dissolved in ethyl alcohol (50 ml) and a catalytic amount of paradium on carbon was added thereto. The mixture was stirred at room temperature for 3 hours under hydrogen atmosphere. After completion of the reaction, the catalyst was filtered off and the solvent in the filtrate was distilled off under reduced pressure to give a quantitative amount of L-leucyl-L-norleucinol. Water (20 ml) and potassium carbonate (2.2 g) and then carboethoxyphthalimide (1.6 g) were added thereto and the mixture was stirred at room temperature for 2 hours. After completion of the reaction, the mixture was extracted with ethyl acetate three times and the extract was washed with brine, followed by drying over anhydrous magnesium sulfate. Ethyl acetate was distilled off under reduced pressure. When the residue was purified by medium-pressure column chromatography using silica gel, the titled N-phthaloyl-L-leucyl-L-norleucinol (0.5 g, crystal) was obtained.

(d) Preparation of N-phthaloyl-L-leucyl-L-norleucinal

N-phthaloyl-L-leucyl-L-norleucinol (0.5 g) prepared in step (c) and triethylamine (0.7 g) were dissolved in anhydrous dimethyl sulfoxide (6 ml). A solution of sulfur trioxide-pyridine complex (1.0 g) in dimethyl sulfoxide (6 ml) was added thereto. After stirring for 10 minutes at room temperature, the mixture was poured into ice water (100 ml), which was then extracted 3 times with ethyl acetate. The extract was washed with 10% citric acid, brine, saturated sodium hydrogencarbonate, and brine, followed by drying over sodium sulfate. Ethyl acetate was distilled off under reduced pressure. When the residue was recrystallized from a mixed solvent of ethyl acetate and hexane, the titled N-phthaloyl-L-leucyl-L-norleucinal (0.3 g, crystal) was obtained.

EXAMPLE 18

Production of N-benzyloxycarbonyl-L-leucyl-L-norleucinal
[compound of formula (1) where $R_1=C_6H_5CH_2OCO-$, $R_2=H-$, $R_3=CH_3(CH_2)_3-$, $R_4=CH_3(CH_2)_3-$]

(a) Preparation of N-benzyloxycarbonyl-L-norleucine

L-norleucine (7.8 g) and potassium carbonate (8.4 g) were dissolved in water (200 ml). To this solution, a solution of benzyloxycarbonyl chloride (12.4 g) in dioxane (20 ml) was added with ice cooling, and the mixture was stirred at room temperature for 8 hours. After the completion of the reaction, the solution was washed with ether, the pH value of the aqueous solution was adjusted to 2 or below with 5N HCl and the solution was extracted with ethyl acetate. When the extract was dried over sodium sulfate and the solvent was concentrated under reduced pressure, the titled N-benzyloxycarbonyl-L-norleucine (9.5 g, oil) was obtained.

(b) Preparation of N-benzyloxycarbonyl-L-norleucyl-L-norleucine methyl ester

N-benzyloxycarbonyl-L-norleucine (7.0 g) obtained in step (a) was dissolved in dry methylene chloride (100 ml). To the solution, 1-ethyl-3-(3-dimethylaminopropyl)carbodiimide hydrochloride (5.4 g) was added. To the resulting solution was added a solution of L-norleucine methyl ester hydrochloride (4.2 g) and triethylamine (5.2 g) in dry methylene chloride (100 ml) and the mixture was stirred at room temperature for 12 hours. After the completion of the reaction, the mixture was washed with 1N HCl, brine, saturated sodium hydrogencarbonate, and brine, followed by drying over sodium sulfate. The solvent was distilled off under reduced pressure. When the residue was purified by medium-pressure column chromatography using silica gel, the titled N-benzyloxycarbonyl-L-norleucyl-L-norleucine methyl ester (8.0 g, crystal) was obtained.

(c) Preparation of N-benzyloxycarbonyl-L-norleucyl-L-norleucinol

N-benzyloxycarbonyl-L-norleucyl-L-norleucine methyl ester (4.0 g) prepared in step (b) and sodium borohydride (1.2 g) were suspended in t-butyl alcohol (100 ml) and the suspension was refluxed (90° C.) under nitrogen atmosphere. Absolute methanol (16 ml) was then added dropwise under reflux. After completion of the dropwise addition, the mixture was stirred under reflux for 30 minutes and restored to room temperature, followed by addition of water (50 ml) with ice cooling. After distilling off methanol and t-butyl alcohol under reduced pressure, the residue was extracted three times with ethyl acetate. The extract was washed with brine and dried over anhydrous magnesium sulfate. After distilling off ethyl acetate under reduced pressure, the residue was purified by medium-pressure column chromatography using silica gel, whereupon the titled N-benzyloxycarbonyl-L-norleucyl-L-norleucinol (2.2 g, crystal) was obtained.

(d) Preparation of N-benzyloxycarbonyl-L-norleucyl-L-norleucinal

N-benzyloxycarbonyl-L-norleucyl-L-norleucinol (1.7 g) prepared in step (c) and triethylamine (1.8 g) were dissolved in anhydrous dimethyl sulfoxide (12 ml). A solution of sulfur trioxide-pyridine complex (3.0 g) in dimethyl sulfoxide (12 ml) was added thereto. After stirring for 10 minutes at room temperature, the mixture was poured into ice water (200 ml), which was then extracted 3 times with ethyl acetate. The extract was washed with 10% citric acid, brine, saturated sodium hydrogencarbonate, and brine, followed by drying over sodium sulfate. Ethyl acetate was distilled off under reduced pressure. When the residue was recrystallized from a mixed solvent of ethyl acetate and hexane, the titled N-benzyloxycarbonyl-L-norleucyl-L-norleucinal (1.2 g, crystal) was obtained.

The physical properties of the compounds in the foregoing examples are summarized in Table 1.

TABLE 1

| Ex. No. | Structure | Physical property $^1$H-NMR (ppm): deuterochloroform, standard: TMS |
|---|---|---|
| 1 | 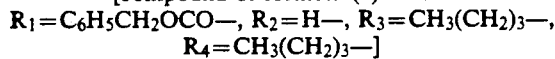 | 0.80–1.20(12H, m), 1.20–2.10 (19H, m), 2.20(2H, t, J=8.0Hz), 4.20–4.70(2H, m), 6.08(1H, d, J=8.0Hz), 6.92(1H, d, J=7.0Hz), 9.54(1H, s) m.p.: 55° C. (decompose) |

TABLE 1-continued

| Ex. No. | Structure | Physical property <br> $^1$H-NMR (ppm): deuterochloroform, standard: TMS |
|---|---|---|
| 2 | (CH$_2$)$_4$–C(=O)–NH–CH(CH$_2$CH(CH$_3$)$_2$)–C(=O)–NH–CH((CH$_2$)$_3$CH$_3$)–CH(=O) with CH$_3$ branch | 0.80–1.10(12H, m), 1.10–2.00 (15H, m), 2.18(2H, t, J=8.0Hz), 4.26(1H, dd, J=8.0 & 12.0Hz), 4.66 (1H, dd, J=8.0 & 14Hz), 6.92(1H, d, J=8.0Hz), 7.82(1H, d, J=8.0Hz), 9.50(1H, s) |
| 3 | (CH$_3$)$_2$CH–CH$_2$–C(=O)–NH–CH(CH$_2$CH(CH$_3$)$_2$)–C(=O)–NH–CH((CH$_2$)$_3$CH$_3$)–CH(=O) | 0.80–1.20(15H, m), 1.20–2.00 (10H, m), 2.00–2.30 (2H, m), 4.20–4.80(2H, m), 6.12(1H, d, J=8.0Hz), 7.00(1H, d, J=7.0Hz), 9.50(1H, s) <br> m.p.: 134° C. (decompose) |
| 4 | (CH$_3$)$_3$C–O–C(=O)–NH–CH(CH$_2$CH(CH$_3$)$_2$)–C(=O)–NH–CH((CH$_2$)$_3$CH$_3$)–CH(=O) | 0.80–1.05(9H, m), 1.20–2.00 (9H, m), 1.46(9H, s), 4.12(1H, dd, J=8.0 & 15Hz), 4.48(1H, dd, J=8.0 & 13Hz), 4.84(1H, d, J=8.0Hz), 6.64 (1H, d, J=7.0Hz), 9.56(1H, s) <br> m.p.: 57° C. (decompose) |
| 5 | adamantyl–O–C(=O)–NH–CH(CH$_2$CH(CH$_3$)$_2$)–C(=O)–NH–CH((CH$_2$)$_3$CH$_3$)–CH(=O) | 0.80–1.10(9H, m), 1.20–2.20 (9H, m), 1.65(6H, broad-s), 2.12(9H, broad-s), 4.14(1H, dd, J=6.0Hz & 14Hz), 4.48 (1H, dd, J=7.0Hz & 13Hz), 4.84(1H, d, J=6.0Hz), 5.64 (1H, d, J=7.0Hz), 9.56(1H, s) |
| 6 | 4-Cl-C$_6$H$_4$–CH$_2$–O–C(=O)–NH–CH(CH$_2$CH(CH$_3$)$_2$)–C(=O)–NH–CH((CH$_2$)$_3$CH$_3$)–CH(=O) | 0.80–1.11(9H, m), 1.10–2.20 (9H, m), 4.20(1H, dd, J=8.0 & 12Hz), 4.48(1H, dd, J=8.0 & 11Hz), 5.06(2H, s), 5.14 (1H, d, J=8.0Hz), 6.44(1H, d, J=8.0Hz), 7.30(4H, s), 9.55(1H, s) <br> m.p.: 93° C. (decompose) |
| 7 | 4-OCH$_3$-C$_6$H$_4$–CH$_2$–O–C(=O)–NH–CH(CH$_2$CH(CH$_3$)$_2$)–C(=O)–NH–CH((CH$_2$)$_3$CH$_3$)–CH(=O) | 0.80–1.00(9H, m), 1.10–2.00 (9H, m), 3.82(3H, s), 4.20(1H, m), 4.48(1H, dd, J=7.0 & 12Hz), 5.04(2H, s), 5.08(1H, d, J=7.0Hz), 6.48(1H, d, J=7.0Hz), 6.86(2H, d, J=9.0Hz), 7.28(2H, d, J=9.0Hz), 9.54(1H, s) <br> m.p.: 87° C. (decompose) |
| 8 | 4-NO$_2$-C$_6$H$_4$–CH$_2$–O–C(=O)–NH–CH(CH$_2$CH(CH$_3$)$_2$)–C(=O)–NH–CH((CH$_2$)$_3$CH$_3$)–CH(=O) | 0.80–1.10(9H, m), 1.10–2.00 (9H, m), 4.20(1H, dd, J=8.0 & 14Hz), 4.52(1H, dd, J=6.0 & 11Hz), 5.20(2H, s), 5.32(1H, d, J=8.0Hz), 6.46, (1H, d, J=6.0Hz), 7.48(2H, d, J=8.0Hz), 8.20(2H, d, J=8.0Hz), 9.56(1H, s) <br> m.p.: 89° C. (decompose) |
| 9 | 2-Cl-C$_6$H$_4$–CH$_2$–O–C(=O)–NH–CH(CH$_2$CH(CH$_3$)$_2$)–C(=O)–NH–CH((CH$_2$)$_3$CH$_3$)–CH(=O) | 0.70–1.10(9H, m), 1.10–2.00 (9H, m), 4.20(1H, m), 4.48(1H, dd, J=6.0 & 13Hz), 5.18(1H, d, J=6.0Hz), 5.24(2H, s), 6.48(1H, d, J=8.0Hz), 7.10–7.50(4H, m), 9.56(1H, s) <br> m.p.: 114° C. (decompose) |

TABLE 1-continued

| Ex. No. | Structure | Physical property<br>¹H-NMR (ppm): deuterochloroform, standard: TMS |
|---|---|---|
| 10 | Cl₃C-CH₂-O-C(=O)-NH-CH(CH₂-CH(CH₃)₂)-C(=O)-NH-CH((CH₂)₃CH₃)-CH(=O) | 0.80–1.00(9H, m), 1.10–2.00 (9H, m), 4.20(1H, dd, J=8.0 & 16Hz), 4.53(1H, dd, J=7.0 & 11Hz), 4.74(2H, s), 5.42(1H, d, J=8.0Hz), 6.40(1H, d, J=7.0Hz), 9.56(1H, s)<br>m.p.: 86° C. (decompose) |
| 11 | (CH₃)₃Si-(CH₂)₂-O-C(=O)-NH-CH(CH₂-CH(CH₃))-C(=O)-NH-CH((CH₂)₃CH₃)-CH(=O) | 0.00(9H, s), 0.80–1.10 (12H, m), 1.10–2.00(9H, m), 4.12(2H, dd, J=8.0 & 10Hz), 4.18(1H, m), 4.44(1H, dd, J=7.0 & 13Hz), 5.13(1H, d, J=7.0Hz), 6.68(1H, d, J=8.0Hz), 9.52(1H, s)<br>Refractive index = 1.4634 |
| 12 | H₃C-C₆H₄-SO₂-NH-CH(CH₂-CH(CH₃)₂)-C(=O)-NH-CH((CH₂)₃CH₃)-CH(=O) | 0.73(3H, d, J=6.0Hz), 0.86 (3H, d, J=6.0Hz), 0.90(3H, t, J=6.0Hz), 1.10–1.90(9H, m), 2.42(3H, s), 3.74(1H, dd, J=8.0 & 13Hz), 4.30(1H, dd, J=7.0 & 14Hz), 5.10(1H, d, J=8.0Hz), 6.46(1H, d, J=7.0Hz), 7.28(2H, d, J=8.0Hz), 7.74(2H, d, J=8.0Hz), 9.54(1H, s)<br>m.p.: 135° C. (decompose) |
| 13 | O₂N-C₆H₄-S-NH-CH(CH₂-CH(CH₃)₂)-C(=O)-NH-CH((CH₂)₃CH₃)-CH(=O) | 0.70–1.10(9H, m), 1.10–2.20 (9H, m), 4.00(1H, m), 4.56(1H, dd, J=7.0 & 13Hz), 4.70(1H, m), 6.56(1H, d, J=7.0Hz), 7.26(1H, m), 7.62(1H, m), 8.02(1H, m), 8.24(1H, m), 9.56(1H, s) |
| 14 | Ph₂P(=S)-NH-CH(CH₂-CH(CH₃)₂)-C(=O)-NH-CH((CH₂)₃CH₃)-CH(=O) | 0.70–1.00(9H, m), 1.00–2.00 (9H, m), 3.40(1H, dd, J=7.0 & 9.0Hz), 3.92(1H, m), 4.26(1H, dd, JNH—Ch=7.0Hz, JPNH=13Hz), 6.64(1H, d, J=7.0Hz), 7.30–7.60(6H, m), 7.70–8.00(4H, m), 9.46(1H, s)<br>Refractive index = 1.5692 |
| 15 | Ph₃C-NH-CH(CH₂-CH(CH₃)₂)-C(=O)-NH-CH((CH₂)₃CH₃)-CH(=O) | 0.70–1.00(9H, m), 1.10–2.00(9H, m), 3.36(1H, m), 4.06(1H, m), 7.10–7.50(15H, m), 9.20(1H, s)<br>m.p.: 123° C. (decompose) |
| 16 | Ph-C(=O)-C(CH₃)=CH-NH-CH(CH₂-CH(CH₃)₂)-C(=O)-NH-CH((CH₂)₃CH₃)-CH(=O) | 0.70–1.10(9H, m), 1.10–2.00 (9H, m), 2.12(3H, s), 4.12(1H, dd, J=8.0 & 16Hz), 4.52(1H, dd, J=8.0 & 13Hz), 5.86(1H, s), 6.60(1H, d, J=8.0Hz), 7.20–7.60(3H, m), 7.70–8.00(2H, m), 9.54 (1H, s), 11.38(1H, d, J=8.0Hz)<br>Refractive index = 1.5614 |

TABLE 1-continued

| Ex. No. | Structure | Physical property $^1$H-NMR (ppm): deuterochloroform, standard: TMS |
|---|---|---|
| 17 | 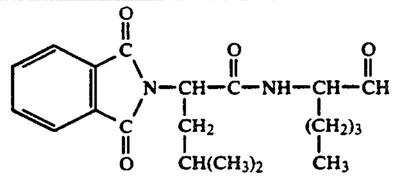 | 0.80–1.10(9H, m), 1.10–2.00(8H, m), 2.40(1H, m), 4.54(1H, dd, J=7.0 & 14Hz), 5.00(1H, dd, J=5.0 & 11Hz), 6.86(1H, d, J=7.0Hz), 7.70–8.00(4H, m), 9.58(1H, s) m.p.: 96° C. (decompose) |
| 18 | 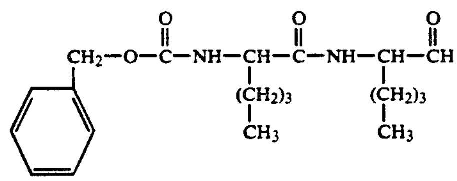 | 0.80–1.00(6H, m), 1.10–2.00(12H, m), 4.20(1H, dd, J=8.0 & 14Hz), 4.52(1H, dd, J=7.0 & 13Hz), 5.12(2H, s), 5.32(1H, d, J=8.0Hz), 6.56(1H, d, J=7.0Hz), 7.38(5H, s), 9.56(1H, s), m.p.: 126° C. (decompose) |

EXAMPLE 19

Production of N-benzyloxycarbonyl-L-leucyl-L-phenylalaninal (SUAM-14541)

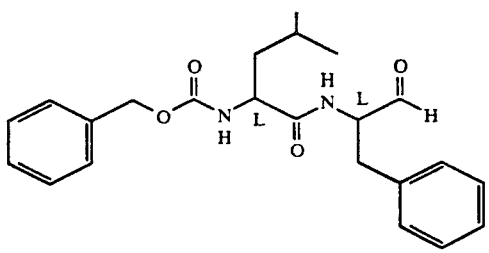

L-phenylalanine ethyl ester hydrochloride (4.6 g, 20 mmol) and N-benzyloxycarbonyl-L-leucine (5.4 g, 20 mmol) were dissolved in dry methylene chloride (100 ml) and triethylamine (2.0 g, 20 mmol) was further added. To this solution, 1-ethyl-3-(3-dimethylaminopropyl)carbodiimide hydrochloride (WSCD) (4.2 g, 22 mmol) was added, and the mixture was stirred at room temperature for one whole day and night. After completion of the reaction, the product was washed successively with 1N HCl, brine, saturated sodium hydrogencarbonate, and brine, followed by drying over sodium sulfate. The solvent was distilled off under reduced pressure. When the residue was purified by medium-pressure column chromatography using silica gel, N-benzyloxycarbonyl-L-leucyl-L-phenylalanine ethyl ester (8.4 g, crystal) was obtained. This product (2.2 g, 5 mmol) and sodium borohydride (570 mg, 15 mmol) were suspended in t-butyl alcohol (50 ml) which was then refluxed (90° C.) under nitrogen atmosphere. Absolute methanol (8 ml) was then added dropwise under reflux. After the addition, the stirring of the mixture under reflux was continued for 1 hour. After the mixture was restored to room temperature, water (30 ml) was added thereto with ice cooling. The methanol and t-butyl alcohol were distilled off under reduced pressure. The residue was extracted with ethyl acetate 3 times, washed with brine and dried over anhydrous magnesium sulfate. When ethyl acetate was distilled off and the residue was purified by medium-pressure column chromatography using silica gel, N-benzyloxycarbonyl-L-leucyl-L-phenylalaninol (1.5 g, crystal) was obtained. This product (1.2 g, 3 mmol) and triethylamine (1.2 g, 12 mmol) were dissolved in anhydrous dimethyl sulfoxide (8 ml). A solution of sulfur trioxidepyridine complex (1.9 g, 12 mmol) in dimethyl sulfoxide (8 ml) was added thereto. After stirring for 10 minutes at room temperature, the mixture was poured into ice water (120 ml), which was then extracted 3 times with ethyl acetate. The extract was washed with 10% citric acid, brine, saturated sodium hydrogencarbonate, and brine, followed by drying over sodium sulfate. Ethyl acetate was distilled off under reduced pressure. When the residue was purified by medium-pressure column chromatography using silica gel, the titled N-benzyloxycarbonyl-L-leucyl-L-phenylalaninal (0.6 g, oil) was obtained.

$^1$H-NMR (in CDCl$_3$, standard TMS): 0.80–1.00 (6H,m), 1.22–1.72 (3H,m), 3.12 (2H,m) 4.16 (1H,m), 4.66 (1H,m), 5.08 (2H,s), 5.12 (1H,m), 5.64 (1H,m), 7.16–7.34 (10H,m), 9.56 (1H,s).

IR spectrum (cm$^{-1}$)(film): 3330, 3270, 3030, 2960, 1730, 1680, 1650, 1530, 1240, 1040, 750, 740, 700.

EXAMPLE 20

Production of N-benzyloxycarbonyl-L-leucyl-L-norleucinal (SUAM-14542)

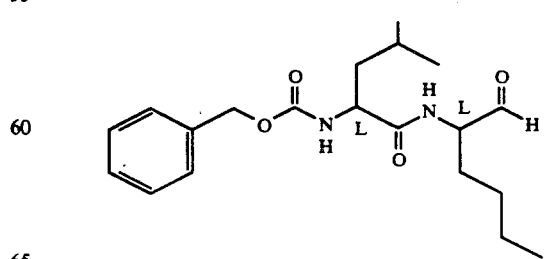

L-norleucine methyl ester hydrochloride (3.6 g, 20 mmol) was replaced for L-phenylalanine ethyl ester hydrochloride and the method of Example 19 was repeated to obtain the titled N-benzyloxycarbonyl-L-leucyl-L-norleucinal (0.5 g, powder), m.p. 93° C.

¹H-NMR (in CDCl₃, standard TMS): 0.80-1.00 (9H,m),
1.22-1.28 (9H,m), 4.12-4.58 (2H,m), 5.12 (2H,s), 5.22 (1H,d,J=8.0), 6.57 (1H, d, J=7.0), 7.36 (5H,s), 9.54 (1H,s).

IR spectrum (cm⁻¹) (KBr): 3320, 3030, 2950, 1720, 1680, 1640, 1530, 1230, 1050, 740, 700.

EXAMPLE 21

Production of
N-benzyloxycarbonyl-L-leucyl-L-methioninal
(SUAM-14543)

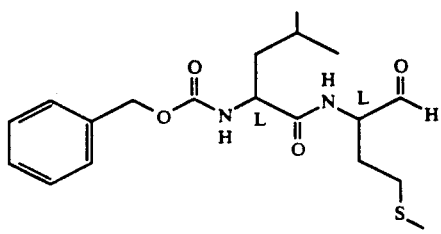

L-methionine methyl ester hydrochloride (4.0 g, 20 mmol) was replaced for L-phenylalanine ethyl ester hydrochloride and the method of Example 19 was repeated to obtain the titled N-benzyloxycarbonyl-L-leucyl-L-methioninal (0.5 g, powder), refractive index (D-line, 25° C.): 1.5342.

¹H-NMR (in DMSO-d₆, standard TMS): 0.94 (6H,d,J=6.0), 1.42-2.58 (5H,m), 2.06 (3H,s), 4.08-4.62 (2H,m), 5.10 (2H,s), 5.37 (1H,d,J=7.0), 6.95 (1H,d,J=6.0), 7.34 (5H,s), 9.56 (1H,d,J=2.0).

IR spectrum (cm⁻¹) (film): 3300, 3070, 2950, 1720, 1700, 1660, 1530, 1240, 1040, 740, 700.

EXAMPLE 22

Production of
N-(4-phenyl)butanoyl-L-leucyl-L-phenylalaninal
(SUAM-14544)

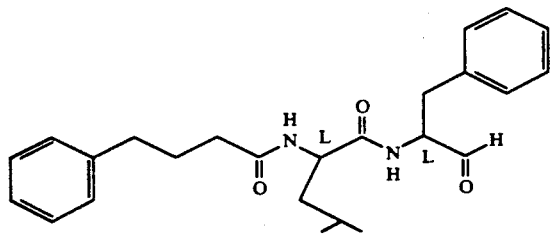

The intermediate product in Example 19, N-benzyloxycarbonyl-L-leucyl-L-phenylalanine ethyl ester (2.2 g, 5 mmol), was dissolved in ethyl alcohol (50 ml) and a small amount of paradium on carbon was added thereto. The mixture was stirred at room temperature for 24 hours under hydrogen atmosphere. After the completion of the reaction, the catalyst was filtered off and the ethyl alcohol was distilled off under reduced pressure. The residue was dissolved in tetrahydrofuran (50 ml) and triethylamine (1.0 g, 10 mmol) was added. To this solution, (4-phenyl)butanoyl chloride (0.9 g, 5 mmol) was added dropwise with ice cooling and the mixture was stirred for 1 hour at the same temperature and for an additional hour after the mixture had been restored to room temperature. After completion of the temperature, tetrahydrofuran was distilled off under reduced pressure, and the residue was dissolved in ethyl acetate (50 ml). The extract was washed successively with 1N HCl, brine, saturated sodium hydrogencarbonate, and brine, followed by drying over anhydrous sodium sulfate. Thereafter, the solvent was distilled off under reduced pressure. When the residue was purified by medium-pressure column chromatography using silica gel, N-(4-phenylbutanoyl)-L-leucyl-L-phenylalanine ethyl ester (2.0 g, crystal) was obtained. This product (1.4 g, 3 mmol) and sodium borohydride (340 mg, 9 mmol) were suspended in t-butyl alcohol (30 ml) which was then refluxed (90° C.) under nitrogen atmosphere. Absolute methanol (5 ml) was then added dropwise under reflux. After the addition, the mixture was stirred under reflux for 1 hour. After the mixture was restored to room temperature, water (30 ml) was added thereto with ice cooling. Methanol and t-butyl alcohol were distilled off under reduced pressure. The residue was extracted with ethyl acetate 3 times, washed with brine and dried over anhydrous magnesium sulfate. When ethyl acetate was distilled off and the residue was purified by medium-pressure column chromatography using silica gel, N-(4-phenyl)butanoyl-L-leucyl-L-phenylalaninol (1.2 g, crystal) was obtained. This product (1.1 g, 2.5 mmol) and triethylamine (1.0 g, 10 mmol) were dissolved in anhydrous dimethyl sulfoxide (8 ml). A solution of sulfur trioxide-pyridine complex (1.6 g, 10 mmol) in dimethyl sulfoxide (8 ml) was added thereto. After stirring for 10 minutes at room temperature, the mixture was poured into ice water (120 ml), which was then extracted 3 times with ethyl acetate. The extract was washed with 10% citric acid, brine, saturated sodium hydrogencarbonate, and brine, followed by drying over sodium sulfate. Ethyl acetate was distilled off under reduced pressure. When the residue was purified by medium-pressure column chromatography using silica gel, the titled N-(4-phenyl)butanoyl-L-leucyl-L-phenylalaninal (0.6 g, oil) was obtained.

¹H-NMR (in CDCl₃, standard TMS): 0.80-1.00 (6H,m), 1.52-2.26 (7H,m), 2.52-2.72 (2H,m), 3.12 (2H,m), 4.40-4.76 (2H,m), 5.72 (1H,d,J=7.0), 6.68(1H,d,J=6.0), 7.14-7.26 (10H,m), 9.58 (1H,s).

IR spectrum (cm⁻¹) (film): 3720, 3060, 2950, 1730, 1630, 1540, 1240, 740, 700.

EXAMPLE 23

Production of
N-(4-phenylbutanoyl)-L-leucyl-L-norleucinal
(SUAM-14545)

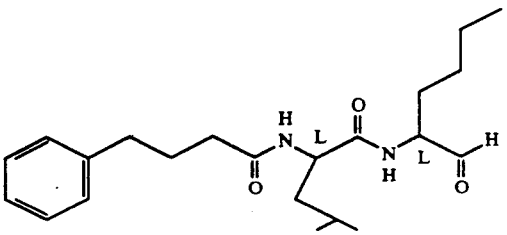

N-benzyloxycarbonyl-L-leucyl-L-norleucine methyl ester (5.3 g, 12 mmol) which is the intermediate product in Example 21 was replaced for N-benzyloxycarbonyl-L-leucyl-L-phenylalanine ethyl ester, the intermediate product in Example 19, and the method of Example 22 was repeated to obtain the titled N-(4-phenylbutanoyl)-L-leucyl-L-norleucinal (0,6 g, oil), refractive index (D-line, 25° C.): 1.5123.

¹H-NMR (in CDCl₃, standard TMS): 0.80–1.00 (6H,m), 1.24–2.32 (13H,m), 2.57–2.72 (2H,m), 4.30–4.63(2H,m), 6.02 (1H,d,J=8.0), 6.28 (1H,d,J=7.0), 7.18–7.23 (5H,m), 9.54 (1H,s).

IR spectrum (cm⁻¹) (film): 3720, 3060, 2950, 1730, 1630, 1540, 1240, 740, 700.

EXAMPLE 24

Production of N-(4-phenyl)butanoyl-L-leucyl-L-methioninal (SUAM-14546)

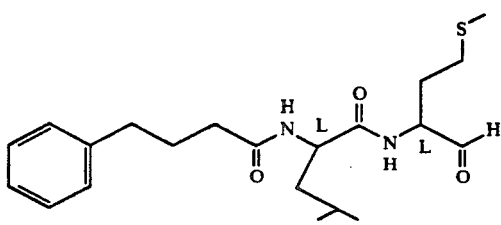

N-benzyloxycarbonyl-L-leucyl-L-methionine methyl ester (2.1 g, 5 mmol) which is the intermediate product in Example 21 was replaced for N-benzyloxycarbonyl-L-leucyl-L-phenylalanine ethyl ester, the intermediate product in Example 19, and the method of Example 22 was repeated to obtain the titled N-(4-phenyl)butanoyl-L-leucyl-L-methioninal (0.5 g, oil), refractive index (D-line, 25° C.): 1.5327.

¹H-NMR (in CDCl₃, standard TMS): 0.80–1.00 (6H,m), 1.40–2.80 (11H,m), 2.03–2.06 (total-3H,both-s), 4.39–4.60 (2H,m), 6.02 (1H,d,J=8.0), 7.18–7.22(6H,m), 9.55 and 9.58(total-1H,both-s).

IR spectrum (cm⁻¹) (film): 3270, 3060, 2950, 1730, 1630, 1540, 1240, 740, 700.

EXAMPLE 25

Production of N-benzyloxycarbonyl-L-leucine 1s-chloroacetyl-2-phenylethylamide (SUAM-11705)

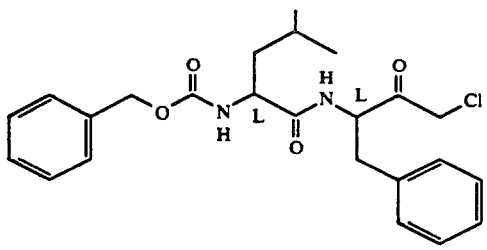

N-benzyloxycarbonyl-L-leucyl-L-phenylalanine ethyl ester (2.6 g, 6 mmol) which is the intermediate product in Example 19 was dissolved in a small volume of methyl alcohol and 1N NaOH (10 ml) was added thereto. The suspension was stirred at room temperature until a clear solution resulted. Methyl alcohol was distilled off under reduced pressure and the residue was partitioned between water and ethyl acetate. The aqueous layer was acidified with 10N HCl, extracted 3 times with ethyl acetate and the organic phase was dried over anhydrous sodium sulfate. After distilling off the solvent under reduced pressure, N-benzyloxycarbonyl-L-leucyl-L-phenylalanine (2.4 g, crystal) was obtained. This product (2.1 g, 5 mmol) was dissolved in dry tetrahydrofran (20 ml). Triethylamine (0.5 g, 5 mmol) was added thereto and the mixture was restored to −10° C. To this solution, ethyl chlorocarbonate (0.6 g, 5 mmol) was added and the mixture was stirred for 20 minutes at −10° C. After the mixture was restored to room temperature, an excess of a diazomethane solution in ether was added and the mixture was stirred for an additional 30 minutes. Gaseous hydrogen chloride was bubbled into the resulting solution for about 10 minutes. After completion of the reaction, the solvent was distilled off. Ethyl acetate (50 ml) was added and the mixture was washed with brine, saturated sodium hydrogencarbonate, and brine, followed by drying over sodium sulfate. When the residue was purified by medium-pressure column chromatography using silica gel, the titled N-benzyloxycarbonyl-L-leucine 1s-chloroacetyl-2-phenylethylamide (1.5 g, crystal), m.p. 140° C. was obtained.

¹H-NMR (in DMSO-d₆, standard TMS): 0.80 (6H,dd,J=4.0, J=7.0), 1.00–1.70 (3H,m), 2.70–3.40 (2H,m), 3.95 (1H,m), 4.45 (2H,dd,J=5.0, J=16.0), 4.50 (1H,m), 5.00 (2H,s), 7.21 (5H,s), 7.28 (5H,s), 7.41 (1H,d,J=8.0), 8.42 (1H,d,J=8.0).

IR spectrum (cm⁻¹) (KBr): 3310, 3280, 2950, 1730, 1685, 1540, 1265, 1240, 700.

EXAMPLE 26

Production of N-benzyloxycarbonyl-L-leucine 1s-chloroacetyl-n-penylamide (SUAM-11706)

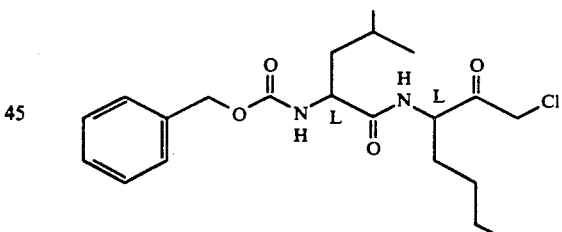

N-benzyloxycarbonyl-L-leucyl-L-norleucine methyl ester (2.4 g, 6 mmol) which is the intermediate product in Example 20 was replaced for N-benzyloxycarbonyl-L-leucyl-L-phenylalanine ethyl ester, the intermediate product in Example 19, and the method of Example 25 was repeated to obtain the titled N-benzyloxycarbonyl-L-leucine 1s-chloroacetyl-n-pentylamide (1.6 g, crystal), m.p. 111° C.

¹H-NMR (in DMSO-d₆, standard TMS): 0.80–1.00 (9H,m), 1.00–1.90 (9H,m), 4.04 (1H,m), 4.30 (1H,m), 4.54 (2H,s), 5.00 (2H,s), 7.36 (5H,s), 7.46 (1H,d,J=8.0), 8.36 (1H,d,J=8.0).

IR spectrum (cm⁻¹) (KBr): 3300, 2950, 1740, 1680, 1660, 1640, 1530, 1280, 1240, 690.

EXAMPLE 27

Production of N-(4-phenylbutanoyl)-L-leucyl-L-norleucyl chloromethyl (SUAM-11707)

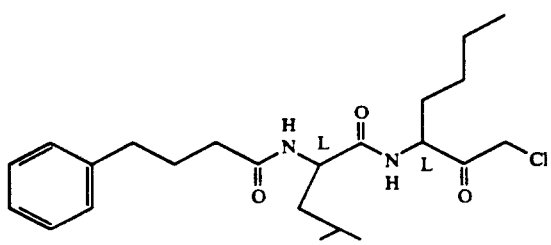

N-(4-phenylbutanoyl)-L-leucyl-L-norleucine methyl ester (2.4 g, 6 mmol) which is the intermediate product in Example 24 was replaced for N-benzyloxycarbonyl-L-leucyl-L-phenylalanine ethyl ester, the intermediate product in Example 19, and the method of Example 25 was repeated to obtain the titled N-(4-phenylbutanoyl)-L-leucyl-L-norleucyl chloromethyl (1.0 g, crystal), m.p. 114° C.

$^1$H-NMR (in DMSO-d$_6$, standard TMS): 0.80–1.00 (9H,m), 1.00–2.40 (15H,m), 4.30 (2H,m), 4.52 (2H,s), 7.20 (5H,s), 8.00 (1H,d,J=8.0), 8.32 (1H,d,J=8.0).

IR spectrum (cm$^{-1}$) (KBr): 3300, 2950, 1730, 1630, 1530, 690.

EXAMPLE 28

Enzyme Inhibitory Activity of the Compounds 19–27 of the Present Invention

The enzyme inhibitory activity of the compounds of the present invention was measured by the following procedures.

Anti-papain Activity

A mixture of a test compound of the present invention, papain (0.015 units) and a citrate buffer solution (20 mM, pH=6.2,1 ml) containing EDTA (0.88 mg) was preincubated at 30° C. for 5 minutes and a substrate solution (1 ml) was added to start the reaction. The substrate was a 1% solution of casein in the citrate buffer. The reaction was performed at 30° C. for 20 minutes. The reaction was quenched by adding 6.5% trichloroacetic acid (3 ml) to the reaction solution. The amount of casein that had been hydrolyzed enzymatically in the trichloroacetic acid soluble fraction was measured by the Lowry-Folin method and the inhibitory activity of the test compound was determined by comparison with the control solution.

Anti-calpain Activity

A mixture of a test compound of the present invention calpain I or II (0.33 units) and an imidazole-HCl buffer solution (50 mM, pH=7.5, 1 ml) containing calcium chloride (0.22 mg) was preincubated at 30° C. for 5 minutes and a substrate solution (1 ml) was added to start the reaction. The substrate was a 0.4% solution of casein in the imidazole-HCl buffer. The reaction was performed at 30° C. for 30 minutes. The reaction was quenched by adding 5% trichloroacetic acid (3 ml) to the reaction solution. The amount of casein that had been hydrolyzed enzymatically in the trichloroacetic acid soluble fraction was measured by the Ross-Schatz method and the inhibitory activity of the test compound was determined by comparison with the control solution.

The so determined activities of the test compounds (19–27) of the present invention against papain and calpain (I and II) are summarized in Tables 2–4.

TABLE 2

| Inhibitory activity toward papain | |
| --- | --- |
| Example No. | Inhibitory activity, IC$_{50}$ (M) |
| 22 | $1.8 \times 10^{-8}$ |
| 23 | $1.5 \times 10^{-8}$ |
| 24 | $1.9 \times 10^{-8}$ |
| 26 | $1.2 \times 10^{-8}$ |
| 27 | $2.5 \times 10^{-8}$ |
| Leupeptin | $5.3 \times 10^{-8}$ |

TABLE 3

| Inhibitory activity toward calpain I | |
| --- | --- |
| Example No. | Inhibitory activity, IC$_{50}$ (M) |
| 19 | $1.0 \times 10^{-7}$ |
| 20 | $5.2 \times 10^{-8}$ |
| 23 | $4.0 \times 10^{-8}$ |
| 24 | $3.8 \times 10^{-8}$ |
| 26 | $1.5 \times 10^{-7}$ |
| 27 | $7.1 \times 10^{-8}$ |
| Leupeptin | $2.1 \times 10^{-7}$ |

TABLE 4

| Inhibitory activity toward calpain II | |
| --- | --- |
| Example No. | Inhibitory activity, IC$_{50}$ (M) |
| 19 | $3.5 \times 10^{-8}$ |
| 20 | $3.4 \times 10^{-8}$ |
| 21 | $2.5 \times 10^{-8}$ |
| 22 | $2.9 \times 10^{-8}$ |
| 23 | $3.2 \times 10^{-7}$ |
| 24 | $7.1 \times 10^{-8}$ |
| 26 | $1.2 \times 10^{-7}$ |
| 27 | $1.4 \times 10^{-7}$ |
| Leupeptin | $9.4 \times 10^{-7}$ |

EXAMPLE 29

Enzyme Inhibitory Activity of the Compounds 1–18 of the Present Invention

The enzyme inhibitory activity of the compounds of the present invention was measured by the following procedures.

Anti-papain Activity

A mixture of a test compound of the present invention, papain (0.015 units) and a citrate buffer solution (20 mM, pH=6.2, 1 ml) containing EDTA (0.88 mg) was preincubated at 30° C. for 5 minutes and a substrate solution (1 ml) was added to start the reaction. The substrate was a 1% solution of casein in the citrate buffer. The reaction was performed at 30° C. for 20 minutes. The reaction was quenched by adding 6.5% trichloroacetic acid (3 ml) to the reaction solution. The amount of casein that had been hydrolyzed enzymatically in the trichloroacetic acid soluble fraction was measured by the Lowry-Folin method and the inhibitory activity of the test compound was determined by comparison with the control solution.

Anti-calpain Activity

A mixture of a test compound of the present invention calpain I or II (0.33 units) and an imidazole-HCl buffer solution (50 mM, pH=7.5, 1 ml) containing calcium chloride (0.22 mg) was preincubated at 30° C. for 5 minutes and a substrate solution (1 ml) was added to start the reaction. The substrate was a 0.4% solution of casein in the imidazole-HCl buffer. The reaction was performed at 30° C. for 30 minutes. The reaction was quenched by adding 5% trichloroacetic acid (3 ml) to the reaction solution. The amount of casein that had been hydrolyzed enzymatically in the trichloroacetic acid soluble fraction was measured by the Ross-Schatz method and the inhibitory activity of the test compound was determined by comparison with the control solution.

Anti-cathepsin Activity

A mixture of a test compound of the present invention and an acetate buffer solution (25 mM, pH=5.1, with 1 mM EDTA, 3.15 ml) containing a substrate (benzyloxycarbonyl-L-lysine-p-nitrophenyl ester, 0.114 mg) was preincubated at 30° C. for 1 minute. To the mixture, a solution (0.05 ml) of cathepsin B (derived from bovine spleen; product of Sigma; 0.05 units) in the acetate buffer was added to start the reaction. Immediately after the start of reaction, the change in absorbance at 326 nm was measured and the inhibitory activity of the test compound was determined by comparison with the control solution.

The so determined activities of the test compounds 1–18 of the present invention against papain and calpain (I and II) are summarized in Tables 5–8. In some of these tables, compound of Example 20 was included as a comparative compound.

TABLE 5

| Inhibitory activity toward papain | |
|---|---|
| Example No. | Inhibitory activity, IC$_{50}$ (M) |
| 3 | 1.2 × 10$^{-7}$ |
| 5 | 2.1 × 10$^{-7}$ |
| 6 | 5.8 × 10$^{-8}$ |
| 7 | 2.5 × 10$^{-7}$ |
| 8 | 3.1 × 10$^{-8}$ |
| 9 | 1.6 × 10$^{-7}$ |
| 10 | 2.6 × 10$^{-7}$ |
| 12 | 1.8 × 10$^{-7}$ |
| 14 | 1.7 × 10$^{-7}$ |
| 16 | 9.6 × 10$^{-8}$ |
| 20 | 3.1 × 10$^{-7}$ |

TABLE 6

| Inhibitory activity toward calpain I | |
|---|---|
| Example No. | Inhibitory activity, IC$_{50}$ (M) |
| 1 | 1.6 × 10$^{-7}$ |
| 3 | 1.0 × 10$^{-7}$ |
| 4 | 3.0 × 10$^{-8}$ |
| 5 | 1.5 × 10$^{-7}$ |
| 6 | 8.7 × 10$^{-8}$ |
| 7 | 1.0 × 10$^{-7}$ |
| 8 | 9.2 × 10$^{-8}$ |
| 9 | 1.1 × 10$^{-7}$ |
| 10 | 9.6 × 10$^{-8}$ |
| 12 | 1.1 × 10$^{-7}$ |
| 14 | 9.0 × 10$^{-8}$ |
| 16 | 4.0 × 10$^{-7}$ |
| 18 | 7.0 × 10$^{-7}$ |

TABLE 6-continued

| Inhibitory activity toward calpain I | |
|---|---|
| Example No. | Inhibitory activity, IC$_{50}$ (M) |
| 20 | 7.1 × 10$^{-7}$ |

TABLE 7

| Inhibitory activity toward calpain II | |
|---|---|
| Example No. | Inhibitory activity, IC$_{50}$ (M) |
| 3 | 1.3 × 10$^{-7}$ |
| 4 | 1.2 × 10$^{-7}$ |
| 7 | 1.3 × 10$^{-7}$ |
| 6 | 1.3 × 10$^{-7}$ |
| 7 | 1.3 × 10$^{-7}$ |
| 8 | 1.3 × 10$^{-7}$ |
| 9 | 1.3 × 10$^{-7}$ |
| 14 | 1.2 × 10$^{-7}$ |
| 20 | 1.3 × 10$^{-7}$ |

TABLE 8

| Inhibitory activity toward cathepsin B | |
|---|---|
| Example No. | Inhibitory activity, IC$_{50}$ (M) |
| 1 | 1.1 × 10$^{-7}$ |
| 2 | 9.2 × 10$^{-6}$ |
| 3 | 5.1 × 10$^{-7}$ |
| 4 | 5.8 × 10$^{-8}$ |
| 5 | 1.8 × 10$^{-7}$ |
| 6 | 7.0 × 10$^{-8}$ |
| 7 | 1.5 × 10$^{-7}$ |
| 8 | 9.9 × 10$^{-8}$ |
| 9 | 1.4 × 10$^{-7}$ |
| 10 | 3.3 × 10$^{-7}$ |
| 11 | 9.6 × 10$^{-7}$ |
| 12 | 1.2 × 10$^{-6}$ |
| 14 | 7.9 × 10$^{-8}$ |
| 15 | 3.2 × 10$^{-5}$ |
| 16 | 7.0 × 10$^{-6}$ |
| 17 | 1.0 × 10$^{-4}$ |
| 18 | 1.1 × 10$^{-7}$ |

The peptide derivative compounds of the present invention which are represented by the formula (1) can be easily synthesized. The strongly inhibit papain, calpain and cathepsin B and hence are anticipated to exhibit inhibitory activity against other cysteine proteinases such as cathepsins H and L. It is also expected that these compounds will exhibit therapeutic effects on various diseases including inflammations that may be presumed to be caused by these cysteine proteinases, as well as cataracts, epidermolysis bullosa, pemphigus and smallpox. Another potential application of these compounds is in purification of cysteine proteinases on an affinity column using these compounds as ligands. The compounds also have a great potential for application as reagents in other biochemical and enzymological fields.

What is claimed is:

1. A compound of the general formula (1):

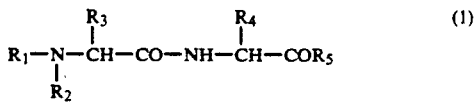

where $R_1$ is a benzyloxycarbonyl group or a 4-phenylbutanoyl group; $R_2$ is a hydrogen atom; $R_3$ is an isobutyl group or an isopropyl group; $R_4$ is a butyl group, a benzyl group or a methylthioethyl group; and $R_5$ is a hydrogen atom or a chloromethyl group.

2. N-benzyloxycarbonyl-L-leucyl-L-norleucinal.